United States Patent
Lura et al.

(10) Patent No.: US 10,888,648 B2
(45) Date of Patent: Jan. 12, 2021

(54) DIALYSIS PRIMING STEPS USING AN INFUSATE CADDY

(71) Applicant: Medtronic, Inc., Minneapolis, MN (US)

(72) Inventors: David B. Lura, Maple Grove, MN (US); Christopher M. Hobot, Tonka Bay, MN (US); Martin T. Gerber, Maple Grove, MN (US); Thomas E. Meyer, Stillwater, MN (US)

(73) Assignee: Medtronic, Inc, Minneapolis, MN (US)

( * ) Notice: Subject to any disclaimer, the term of this patent is extended or adjusted under 35 U.S.C. 154(b) by 90 days.

(21) Appl. No.: 15/219,187

(22) Filed: Jul. 25, 2016

(65) Prior Publication Data
US 2017/0021086 A1    Jan. 26, 2017

Related U.S. Application Data

(60) Provisional application No. 62/196,901, filed on Jul. 24, 2015.

(51) Int. Cl.
*A61M 1/36* (2006.01)
*A61M 1/16* (2006.01)

(52) U.S. Cl.
CPC .......... *A61M 1/3649* (2014.02); *A61M 1/169* (2013.01); *A61M 1/1656* (2013.01)

(58) Field of Classification Search
None
See application file for complete search history.

(56) References Cited

U.S. PATENT DOCUMENTS

| | | | |
|---|---|---|---|
| 1,663,723 | A | 9/1928 | William |
| 4,747,822 | A | 5/1988 | Peabody |
| 4,950,230 | A | 8/1990 | Kendell |
| 5,032,265 | A | 7/1991 | Jha |
| 5,141,493 | A | 8/1992 | Jacobsen |
| 5,643,201 | A | 7/1997 | Peabody |
| 5,744,031 | A | 4/1998 | Bene |
| 6,355,161 | B1 | 3/2002 | Shah |

(Continued)

FOREIGN PATENT DOCUMENTS

| | | |
|---|---|---|
| CN | 202105667 | 1/2012 |
| DE | 202014104252 | 12/2015 |

(Continued)

OTHER PUBLICATIONS

Internation Preliminary Report on Patentability, Application PCT/US2016/043948, dated Jul. 17, 2017.

(Continued)

*Primary Examiner* — Jonathan M Peo
(74) *Attorney, Agent, or Firm* — Roger Hahn; Hahn & Associates

(57) ABSTRACT

The invention relates to devices, systems, and methods for priming, disinfecting, and preparing dialysate and related fluids for use in dialysis. The dialysate and related fluids can be prepared from solutes obtained from infusate containers seated in an infusate caddy. The infusate caddy can be removably positioned in a receiving compartment of a dialysis machine. Similarly, the infusate containers containing the necessary solutes for preparing the dialysate and related fluids can also be removably positioned in the infusate caddy.

22 Claims, 11 Drawing Sheets

(56) References Cited

U.S. PATENT DOCUMENTS

| | | | |
|---|---|---|---|
| 6,645,191 B1 * | 11/2003 | Knerr | A61J 1/2093 604/410 |
| 2002/0091371 A1 | 7/2002 | Ritter | |
| 2005/0242034 A1 * | 11/2005 | Connell | A61M 1/16 210/646 |
| 2010/0051552 A1 * | 3/2010 | Rohde | A61M 1/1656 210/647 |
| 2010/0078092 A1 | 4/2010 | Weilhoefer | |
| 2010/0312172 A1 | 12/2010 | Hoffman | |
| 2011/0017665 A1 | 1/2011 | Updyke | |
| 2011/0189048 A1 * | 8/2011 | Curtis | A61M 1/14 422/3 |
| 2011/0249916 A1 | 10/2011 | Herrenbauer | |
| 2012/0199205 A1 | 8/2012 | Eyrard | |
| 2013/0001165 A1 | 1/2013 | Pohlmeier | |
| 2013/0015302 A1 | 1/2013 | Orter et al. | |
| 2013/0062265 A1 | 3/2013 | Balschat | |
| 2013/0199998 A1 * | 8/2013 | Kelly | A61M 1/1696 210/646 |
| 2014/0018727 A1 | 1/2014 | Burbank | |
| 2014/0217029 A1 | 8/2014 | Meyer | |
| 2017/0021076 A1 | 1/2017 | Lura | |
| 2017/0021079 A1 | 1/2017 | Lura | |
| 2017/0021086 A1 | 1/2017 | Lura | |

FOREIGN PATENT DOCUMENTS

| | | | |
|---|---|---|---|
| EP | 0714668 | 6/1996 | |
| EP | 2735322 | 5/2014 | |
| JP | 2006325668 A | 12/2006 | |
| WO | 9937342 A1 | 7/1999 | |
| WO | 0057935 | 10/2000 | |
| WO | WO-0057935 A1 * | 10/2000 | A61L 2/0023 |
| WO | WO2000057935 A1 | 10/2000 | |
| WO | WO200904984 | 5/2009 | |
| WO | 2011113572 A1 | 9/2011 | |
| WO | 2012138604 A2 | 10/2012 | |
| WO | WO 2013077844 | 5/2013 | |
| WO | 2014121158 A1 | 8/2014 | |
| WO | 2015071247 A1 | 5/2015 | |
| WO | WO 2017004449 | 1/2017 | |
| WO | WO2017/09640 A1 | 2/2017 | |
| WO | WO2017/019640 A1 | 5/2020 | |

OTHER PUBLICATIONS

Written Opinion, Application PCT/US2016/043935, dated Jun. 21, 2017.
International Preliminary Report on Patentability, Appliaction PCT/US2016/043950, dated Jul. 31, 2017.
International Preliminary Report on Patentability, Appliaction PCT/US2016/043935, dated Jul. 17, 2017.
Written Opinion, Application PCT/2016/043948, dated Feb. 2, 2017.
Written Opinion, Application PCT/US2016/043935, dated Feb. 2, 2017.
International Search Report, Application PCT/US2016/043948, dated Feb. 2, 2017.
International Search Report, Application PCT/US2016/043935, dated Feb. 2, 2017.
PCTUS2017025876 International Search Report dated Jun. 29, 2017.
PCT/US2017/025868 Written Opinion dated Jun. 29, 2017.
PCTUS2017025858 International Search Report dated Jun. 29, 2017.
PCTUS2017025858 Written Opinion dated Jun. 29, 2017.
PCTUS2017025876 Written Opinion dated Jun. 29, 2017.
PCT/US2017/025868 International Search Report dated Jun. 29, 2017.
Int'l Search Report PCT/US217/032337.
European Office Action for App. No. 16757383.1, dated Mar. 13, 2020.
Chinese Office Action for App. No. 201680041414.6, dated Jun. 9, 2020.
European Office Action for App. No. 17724468.8, dated May 14, 2020.
Chinese Office Action for App. No. 201680041324.7, dated Jun. 1, 2020.
Chinese Office Action for App. No. 201680041413.1, dated May 28, 2020.
European Search Report for App. No. 16760215.0, dated May 7, 2020.
European Search Report for App. No. 17724689.9, dated May 14, 2020.
Chinese Office Action for App. No. 201680041414.6, dated Oct. 20, 2020.

* cited by examiner

DIALYSIS PRIMING STEPS USING AN INFUSATE CADDY

FIELD OF THE INVENTION

The invention relates to devices, systems, and methods for priming, disinfecting, and preparing dialysate and related fluids for use in dialysis. The dialysate and related fluids can be prepared from solutes obtained from infusate containers seated in an infusate caddy. The infusate caddy can be removably positioned in a receiving compartment of a dialysis machine. Similarly, the infusate containers containing the necessary solutes for preparing the dialysate and related fluids can also be removably positioned in the infusate caddy.

BACKGROUND

Dialysis systems require specified amounts of solutions to be used during each dialysis session, such as sodium chloride, sodium bicarbonate and cation infusates. Further, many cations, such as potassium, calcium and magnesium, can cross the dialyzer and be removed from a patient during dialysis. These cations must be added back into the dialysate to maintain the concentration of these cations at a desired level. Sodium bicarbonate can be used during dialysis as a buffer to control the pH of the dialysate and to treat acidosis by delivering bicarbonate across the dialysis membrane to the patient receiving a treatment. The amounts of sodium chloride, sodium bicarbonate, and other cations added to dialysate should be closely monitored and controlled. Further, the amounts of each of these solutions can vary considerably.

Systems and methods for ensuring proper priming and disinfection of a dialysis machine or related flow paths are required before and after dialysis. The system and methods should be adapted to the solutes added and removed from the dialysate. To facilitate use of dialysis by personnel having varying levels of skill, systems and methods are needed that can ensure that each of the materials to be added to the dialysis system is connected to the correct pumps, valves and connectors of the dialysis system and that proper priming and disinfection is used. Further, there is a need for systems and methods that can ensure that all necessary materials are connected to the dialysis system and at correct locations to enable proper priming and disinfection. There is a further need for methods and systems that can ensure proper disinfection of a dialysis system after a dialysis session is complete. There is a need for a system that can allow users of varying skill levels to easily configure the dialysis session for disinfection, and ensure that the dialysis system can be used outside of a standard dialysis clinic setting, such as in a patient's home. To prepare a dialysis system for use, the dialysis system must be primed with fluid for use as a dialysate. The need includes specific concentrations of sodium chloride and sodium bicarbonate. Hence, there is a need for a system and methods to prime an infusate caddy, and to use the infusate caddy to prime a dialysis system and prepare a dialysate for use in therapy.

SUMMARY OF THE INVENTION

The invention relates to a method of priming a dialysis machine. In any embodiment of the invention, the method can include fluidly connecting one or more detachable container seated in a removable infusate caddy; selectively opening or closing one or more valves to form a priming flow path in the dialysis machine; pumping water using one or more pumps into the priming flow path and through a detachable fluid connector into one or more detachable container containing one or more solutes; dissolving the solutes in the container to form a solution of the solutes inside the container or adding water to the container to form a solution of the solutes inside the container; selectively opening or closing one or more valves to form a dialysate flow path in the dialysis machine; and pumping the solution from the container into the dialysate flow path to prime the dialysis machine with the one or more solutes.

In any embodiment, the infusate caddy can be detachable from the dialysis machine.

In any embodiment, the one or more containers include any one or more group comprising a sodium chloride container, a sodium bicarbonate container and a cation infusate container.

In any embodiment, the step of pumping the solution from the container into the dialysate flow path can include pumping fluid from the sodium chloride container and/or the sodium bicarbonate container to the dialysate flow path upstream of a sorbent cartridge.

In any embodiment, the step of pumping the solution from the sodium chloride container and/or the sodium bicarbonate container to the dialysate flow path can include determining an amount of sodium chloride and/or sodium bicarbonate pumped to the dialysate flow path upstream of the sorbent cartridge.

In any embodiment, the step of determining an amount of sodium chloride and/or sodium bicarbonate pumped to the dialysate flow path can include determining the amount of sodium chloride and/or sodium bicarbonate pumped with a conductivity sensor upstream of the sorbent cartridge.

In any embodiment at least one container can be a disinfection container.

In any embodiment, the disinfection container can contain citric acid.

In any embodiment, prior to the step of pumping water into the priming flow path, the fluid connectors can be filled with a disinfectant solution.

In any embodiment, the method can include the step of selectively opening or closing one or more valves to pump water from the dialysate flow path to the sodium chloride container.

In any embodiment, the method can include partially filling the sodium chloride container with water; wherein a volume of air remains in the sodium chloride container.

In any embodiment, the method can include the step of selectively opening or closing one or more valve to flow air from the sodium chloride container to the dialysate flow path while filling the sodium chloride container with water.

In any embodiment, the method can include the step of selectively opening or closing one or more valves and one or more pumps to pump the solution from the sodium chloride container into the dialysate flow path.

In any embodiment, the amount of solution pumped from the sodium chloride container to the dialysate flow path can be between 10 mL-500 mL.

In any embodiment, the sodium chloride container can be connected to at least two fluid connectors, the fluid connectors each with one or more valve, and the fluid connectors can be connected to the dialysate flow path; and the method can include the step of selectively opening or closing one or more valves to flow air from the sodium chloride container to the dialysate flow path while pumping water from the dialysate flow path to the sodium chloride container.

In any embodiment, the method can include the step of selectively opening or closing one or more valves to pump water from the dialysate flow path to the sodium bicarbonate container.

In any embodiment, the method can include partially filling the sodium bicarbonate container with water; wherein a volume of air remains in the sodium bicarbonate container.

In any embodiment, the amount of fluid pumped from the dialysate flow path to the sodium bicarbonate container can be between 10 mL-4,000 mL.

In any embodiment, the sodium bicarbonate container can be connected to at least two fluid connectors, the fluid connectors each with one or more valve, and the fluid connectors can be connected to the dialysate flow path, and the method can include the step of selectively opening or closing one or more valves to pump water from the dialysate flow path to the sodium bicarbonate container while fluid is pumped from the sodium bicarbonate container to the dialysate flow path.

In any embodiment, the method can include the step of selectively opening or closing one or more valves to pump fluid from the sodium bicarbonate container to the dialysate flow path.

In any embodiment, one or more of the containers can initially contain a solid solute.

In any embodiment, the method can include the step of selectively opening or closing one or more valves and one or more pumps to pump water to the container containing a solid solute to make a solute solution of known concentration.

In any embodiment, the method can include the step of selectively opening or closing one or more valves to prevent the disinfection solution from entering the containers.

In any embodiment, the disinfection solution can be a citric acid solution.

In any embodiment, the steps of pumping fluid from the sodium chloride container to the dialysate flow path and pumping fluid from the sodium bicarbonate container to the dialysate flow path can include generating a dialysis fluid with a concentration of solutes suitable for use in dialysis.

In any embodiment, the step of pumping water into the one or more detachable container can include partially filling the detachable container with water, such that a volume of air is present in a top section of the at least one container.

In any embodiment, the volume of air can prevent an uncontrolled flow of solution out of the at least one container into another container or the dialysate flow path.

In any embodiment, the caddy can include fitting features so that each container can only occupy a unique position within the caddy, wherein the position of each container is aligned with each fluid connector.

In any embodiment, the method can include initiating a dialysis session after priming the dialysis machine, and selectively opening or closing one or more valves and one or more pumps to deliver treatment solutes during the dialysis session with the one or more solutes.

Any of the features disclosed as being part of the invention can be included in the invention, either alone or in combination.

DETAILED DESCRIPTION OF THE INVENTION

Figure 1:
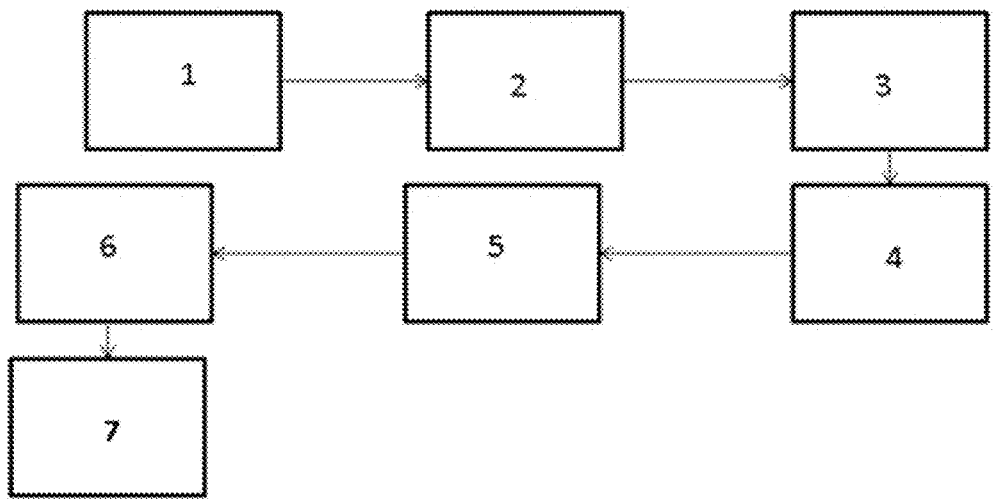
FIG. 1 is a flow chart showing the steps for priming an infusate caddy and priming a dialysis system with fluids from the infusate caddy.

Unless defined otherwise, all technical and scientific terms used generally have the same meaning as commonly understood by one of ordinary skill in the art.

The articles "a" and "an" are used to refer to one or to over one (i.e., to at least one) of the grammatical object of the article. For example, "an element" means one element or over one element.

"Aligned" or "in alignment" refer to two connectable components that are positioned so that a connection can be formed between the components.

The term "amount" of a substance can refer to the mass, concentration, or number of moles of the substance.

The term "bicarbonate container" or "sodium bicarbonate container" refers to a container that can be a stand-alone container or alternatively can be integrally formed with an apparatus for hemodialysis, hemodiafiltration, or hemofiltration. The bicarbonate container can store a source of buffering material, such as sodium bicarbonate, and can be configured to interface with at least one other functional module found in systems for hemodialysis, hemodiafiltration, or hemofiltration. The bicarbonate container can contain at least one fluid pathway and include components such as conduits, valves, filters or fluid connection ports. The bicarbonate container may be single use, or may be refilled and used multiple times, for example, by refilling the bicarbonate container to replace the bicarbonate material which can be a liquid or solid form.

The term "bottom section" of a container refers to a part of a container at a lower elevation.

The term "cation infusate container" or "infusate container" refers to a source from which cations can be obtained. Examples of cations include, but are not limited to, calcium, magnesium and potassium. The source can be a solution containing cations or dry compositions that are hydrated by the system. The cation infusate container is not limited to cations and may optionally include other substances to be infused into a dialysate or replacement fluid; non-limiting examples can include glucose, dextrose, acetic acid and citric acid.

A "citric acid solution" is a solution containing citric acid, $C_6H_8O_7$, dissolved in water.

The term "comprising" includes, but is not limited to, whatever follows the word "comprising." Use of the term indicates the listed elements are required or mandatory but that other elements are optional and may be present.

A "conductivity sensor" is a sensor that can measure the conductivity of a fluid.

A "connector" and "for connection" describe forming a fluid connection between two components wherein fluid or gas can flow from one component, through a connector or a component for connection, to another component. The connector provides for a fluid connection in its broadest sense and can include any type of tubing, fluid or gas passageway, or conduit between any one or more components of the invention.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "contain" means to hold any solid, liquid or component within a container.

The term "container" is a receptacle that may be flexible or inflexible for holding any fluid or solid, such as a spent dialysate fluid, or a sodium chloride or sodium bicarbonate solution or solid, or urease, or urease/alumina.

The terms "deliver" or "delivering" refer to movement of a solute, fluid, or gas from a first location to a second location.

The term "detachable" or "detached" relates to any component of the present invention that can be separated from a system, module, cartridge or any component of the invention. "Detachable" can also refer to a component that can be taken out of a larger system with minimal time or effort. In certain instances, the components can be detached with minimal time or effort, but in other instances can require additional time or effort. The detached component can be optionally reattached to the system, module, cartridge or other component. A detachable module can often be part of a reusable module.

The terms "determining" and "determine" refer to ascertaining a particular state of a system or variable(s).

A "dialysate flow path" or "dialysate flow loop" is a route in which a fluid can travel during dialysis.

"Dialysis" or "dialysis therapy" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

A "dialysis machine" is a system comprising a dialyzer, pumps, valves and fluid lines that is used to carry out a dialysis session.

A "disinfection container" is a source from which a disinfection solution, such as citric acid, can be obtained. The source can be a solution containing disinfecting chemicals or dry compositions that are hydrated by the system.

A "disinfection solution" is a solution that can disinfect any component, connector or container of a dialysis system.

The terms "dissolving" or to "dissolve" refer to adding a solvent to a solute such that the solute and solvent generate a solution.

The terms "filling" or to "fill" refer to the addition of a solid, gas, fluid, or any combination thereof in a container or compartment. Filling a container can include completely filling the container or partially filling the container. As such, "partially filling" will be understood to mean filing a volume to any quantity less than a whole.

A "fitting feature" is any protrusion, indentation, groove, ridge, having any shape, size, or geometry that serves to ensure that only a corresponding fitting feature complementary to the fitting feature is capable of forming a connection or fit to the corresponding fitting feature. The fitting feature also includes non-mechanical means for ensuring complementary connection such as magnets placed at particular locations, or visual or aural indicators such as color, lettering, or sound. The fitting feature can be affixed, integral, or labeled on a component or surface to ensure that a corresponding feature on a desired component or surface can mate or connect to the component or surface having the fitting feature.

A "fluid" is a liquid substance optionally having a combination of gas and liquid phases in the fluid. Notably, a liquid can therefore also have a mixture of gas and liquid phases of matter.

The terms "fluidly connect" or "fluidly connecting" refer to the joining of two or more components to form a fluid pathway.

The term "fluid connection," "fluidly connectable" or "fluidly connected" refers to the ability to pass fluid, gas, or mixtures thereof from one point to another point. The two points can be within or between any one or more of compartments, modules, systems, and components, all of any type.

The term "generating a dialysis fluid with a concentration of solutes suitable for use in dialysis" or to "generate a dialysis fluid with a concentration of solutes suitable for use in dialysis" is the process of creating a solution from a solvent and at least one solute, or modifying an existing solution, wherein the concentration of the solute in the generated solution is at a concentration intended for use in a dialysis session.

The term "infusate caddy" or "caddy" refers to a container detachably removable from a dialysis system, the caddy configured to hold one or more other containers. In any embodiment, the caddy can include one or more connectors for fluid connection from the containers to the dialysis system.

An "infusate container" is a container adapted to contain one or more fluids for use in dialysis. The infusate container can at times hold dry chemicals that are later able to be reconstituted with a fluid to form a further useable fluid within the system.

The terms "initiating a dialysis session" or to "imitate a dialysis session" refer to starting a dialysis treatment, session, or therapy for a patient.

The term "known concentration" refers to the amount of a solute dissolved in a solvent, wherein the amount is either predetermined or ascertained.

To "move fluid" refers to operating pumps or valves to cause fluid to travel from one point in a system to another.

The term "partially filling" a container refers to the addition of fluid to a container, wherein the volume of fluid added to the container is less than the volume of the container.

The terms "pathway," "conveyance pathway," "fluid flow path," and "flow path" refer to the route through which a fluid or gas, or both, such as dialysate or blood, travels.

The term "prevent" refers to operation of a system to preclude a particular result.

The term "priming" refers to conveying a liquid into a void volume of a fluid pathway to fill the pathway with liquid.

A "priming flow path" is a fluid flow path configured to convey liquid into a fluid pathway to ready the fluid pathway for use in dialysis.

The term "pump" refers to any device that causes the movement of fluids or gases by applying suction or pressure.

The terms "pumping," "pumped," or to "pump" refers to moving or flowing a fluid using a pump of any type known to those of ordinary skill in the art.

The term "seated" refers to a component positioned on or in a second component.

The term "selectively opening or closing one or more valves" refers to operating one or more valves to control the direction of a fluid, gas or mixture of fluid and gas flowing through a flow path.

The terms "sodium bicarbonate reservoir" and "sodium bicarbonate container" refer to an object that can be a stand-alone enclosure or alternatively can be integrally formed with an apparatus for hemodialysis, hemodiafiltration, or hemofiltration. The object can store a source of sodium bicarbonate in solid and/or solution form, and can be configured to interface with at least one other functional module found in systems for hemodialysis, hemodiafiltration, or hemofiltration. The sodium bicarbonate reservoir or container can contain at least one fluid pathway and include components such as conduits, valves, filters or fluid connection ports.

The terms "sodium chloride reservoir" and "sodium chloride container" refer to an object that can be a stand-alone enclosure or alternatively can be integrally formed with an apparatus for hemodialysis, hemodiafiltration, or hemofiltration. The object can store a source of sodium, such as sodium chloride in solid and/or solution form, and can be configured to interface with at least one other functional module found in systems for hemodialysis, hemodiafiltration, or hemofiltration. The sodium chloride reservoir or container can contain at least one fluid pathway and include components such as conduits, valves, filters or fluid connection ports.

A "solid solute" is a substance in a solid, non-dissolved state, which is intended to be dissolved in a solvent.

A "solute" is a substance dissolved in, or intended to be dissolved in, a solvent.

A "solute solution" is an aqueous solution containing one or more dissolved ionic compounds.

The term "sorbent cartridge" refers to a cartridge containing one or more sorbent materials for removing specific solutes from solution. The term "sorbent cartridge" does not require the contents in the cartridge be sorbent based, and the contents of the sorbent cartridge can be any contents that can remove solutes from a dialysate. The sorbent cartridge may include any suitable amount of one or more sorbent materials. In certain instances, the term "sorbent cartridge" refers to a cartridge which includes one or more sorbent materials besides one or more other materials capable of removing solutes from dialysate. "Sorbent cartridge" can include configurations where at least some materials in the cartridge do not act by mechanisms of adsorption or absorption.

"Suitable for use in dialysis" refers to a state of a fluid wherein the concentration of specific substances in the fluid is within a range that can be safely used during dialysis.

The term "top section" of a part of a volume near or at a highest elevation of a volume.

"Treatment solutes" are solutes that are to be delivered to a patient during therapy.

The term "uncontrolled flow" refers to the movement of a fluid that is not intended.

A "unique position" refers to a specific portion or location of a surface to which a component can be placed. The component can be placed only in the unique position on the surface such as an interior wall of a compartment, and not at other positions within the compartment.

The term "upstream" refers to a position of a first component in a flow path relative to a second component wherein fluid will pass by the first component prior to the second component during normal operation. The first component can be said to be "upstream" of the second component, while the second component is "downstream" of the first component.

A "valve" is a device capable of directing the flow of fluid or gas by opening, closing or obstructing one or more pathways to allow the fluid or gas to travel in a path. One or more valves configured to accomplish a desired flow can be configured into a "valve assembly."

A "volume of air" refers to any quantity of gas or mixture of gases.

The term "water," as used herein, refers to any water having an appropriate purity suitable for use in dialysis including hemodialysis, hemodiafiltration, and peritoneal dialysis. Water having an appropriate purity suitable for use in rinseback is also contemplated by the invention.

Infusate Caddy

FIG. 1 shows as series of steps for priming a dialysis machine and related flow paths using an infusate caddy and steps to create dialysate for use in any one of hemodialysis, hemodiafiltration, or rinseback. In step 1, the infusate caddy is seated in a receiving compartment of a dialysis machine and fluidly connected to a dialysis machine. The infusate caddy can contain or receive one or more infusate containers for dialysis, including any one of a sodium chloride container, a sodium bicarbonate container, a cation infusate container, and combinations thereof, as well as containers for cleaning the system, such as a citric acid container. The infusate containers are separate components and are intended to be placed inside and removed out of the infusate caddy. In one non-limiting, preferred embodiment, the infusate caddy only contains a sodium chloride container, a sodium bicarbonate container, and a cation infusate container. Step 1 further includes connecting each of the infusate containers seated within the infusate caddy to fluid connectors on a dialysis machine. The infusate caddy can be aligned so that each infusate container seated in the infusate caddy can only be connected to a particular fluid connector on the dialysis machine. As such, the infusate caddy can ensure that each of the aligned infusate containers is connected to a specified fluid connector and hence, fluidly connected with the dialysate flow loop at a specified location. A disinfectant solution, such as a citric acid solution can remain in the fluid lines of the dialysis machine and the user can install and connect the infusate system before the citric acid is flushed from the fluid lines of the dialysis machine. In step 2 the residual disinfectant can be removed from the fluid lines of the dialysis machine that connect to the containers seated in the infusate caddy.

The containers in the infusate caddy can initially contain a solid source or a solution of the particular solute, compound, or material to be added to the dialysate flow loop during priming or use of the dialysis system. Before adding fluids to the dialysis system, water can be added to the caddy containers to dissolve the solids to produce a concentrate that can be metered into the dialysate fluid pathway of the dialysis machine. The water can be any water having a suitable purity for use in dialysis. The water can be purified water from a water reservoir attached to the system, or can be water purified by the system using one or more water purification modules, such as a sorbent cartridge. In step 3, water from the dialysate flow path is added to a sodium chloride container to dissolve a portion of the sodium chloride until an approximately saturated solution is produced to generate a sodium chloride solution of known concentration. Alternatively, a known amount of sodium chloride can be placed in the sodium chloride container, and a known amount of water pumped into the sodium chloride container to generate a sodium chloride solution of known concentration. In step 4, the sodium chloride solution is pumped to the dialysate flow loop to prime the dialysate flow loop with a sodium concentration suitable for use in dialysis.

In step 5, water from the dialysate flow loop can be pumped to a sodium bicarbonate container to dissolve a portion of the solid sodium bicarbonate until an approximately saturated solution is produced to generate a sodium bicarbonate solution of a known concentration. Alternatively, a known amount of sodium bicarbonate can be placed in the sodium bicarbonate container, and a known amount of water pumped into the sodium bicarbonate container to generate a sodium bicarbonate solution of known concentration. In step 6, the sodium bicarbonate solution can be pumped to the dialysate flow loop to create a dialysate with a specified sodium bicarbonate and sodium chloride solution suitable for use in dialysis. Selectively opening and closing the pumps and valves described herein can be set to result in the specified sodium bicarbonate and sodium chloride solution.

The amount of water pumped into the sodium bicarbonate container and sodium chloride container to dissolve the sodium bicarbonate solids and sodium chloride solids can depend on the needs of the system and patient, including between 10 mL and 500 mL of fluid in step 3. The concentrate of sodium chloride produced can be around 5.5 M. For systems with a small dialysate flow path, such as 0.5 L, only about 15 mL of sodium chloride concentrate or less will be needed to prime the entire system. For larger systems, and for priming of sorbent cartridges, flush reprocessed dialyzers and for providing a fluid bolus to a patient, large amounts of sodium chloride may be necessary, requiring up to 500 mL of the sodium chloride concentrate. Similarly, between 10 mL-4,000 mL of sodium bicarbonate concentrate may be required. A system with a small dialysate flow path may only require about 10 mL of sodium bicarbonate concentrate for priming. However, for larger systems, and if the patient requires additional bicarbonate, for example, to correct acidosis, a large amount of sodium bicarbonate concentrate may be necessary.

Optionally, in step 7, water can be added from the dialysate flow loop to a cation infusate container seated or received in the infusate caddy, to dissolve a solid source of cation infusates and create an infusate solution of a known concentration. The infusates, or any other treatment solutes, can be added to the dialysate flow loop as needed during dialysis. In any embodiment, step 7 can be performed before step 4, step 5 or step 6. Further, the bicarbonate concentrate and the cation infusate can be metered into the dialysate flow loop concurrently.

Figure 2:
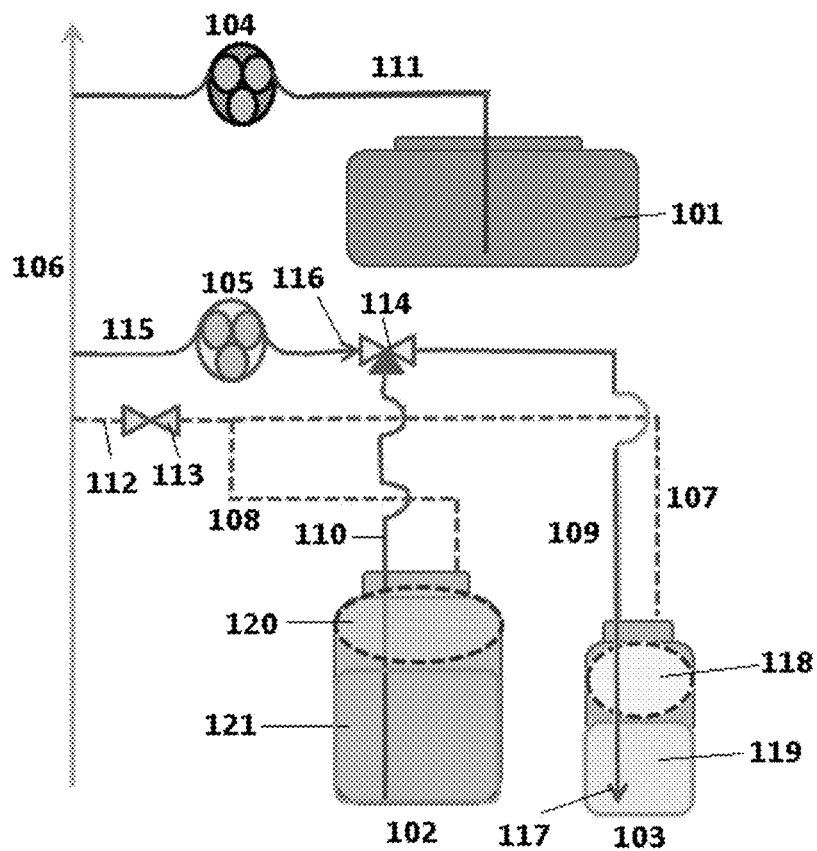
FIG. 2 shows a flow path of the connectors, pumps and valves in an infusate caddy using one two-way valve and one three-way valve controlling fluid to a sodium chloride and sodium bicarbonate container.

FIG. 2 shows a non-limiting flow diagram containing pumps, valves and connectors that can be used with an infusate caddy for performing step 2 as described in FIG. 1. The infusate containers including cation infusate container 101, a sodium bicarbonate container 102, and a sodium chloride container 103 can be seated in the infusate caddy, and then fluidly connected to a dialysate flow path as depicted in FIG. 2. The one or more containers can initially contain a solid, which can be dissolved to create a solution, or a solution for dialysis. For example, the sodium chloride container 103 can contain sodium chloride solids in the bottom section 119 of the sodium chloride container 103. Sodium chloride container 103 can initially be nearly completely filled with sodium chloride solids. Sodium chloride container 103 can be filled only partially with water. As sodium chloride concentrate is metered out of the sodium chloride container 103 during use, additional fluid can be introduced into the sodium chloride container 103, dissolving some of the remaining sodium chloride solids in the bottom section 119 of the container 103, so that the sodium chloride solution remains approximately saturated. The top section 118 of sodium chloride container 103 can contain air due to the fact that sodium chloride container 103 has only been partially filled with water. Similarly, a bottom section 121 of sodium bicarbonate container 102 can initially contain sodium bicarbonate solids or a sodium bicarbonate concentrate. The top section 120 of sodium bicarbonate container 102 can initially contain air. As with the sodim chloride container 103, the sodium bicarbonate container 102 can initially be nearly completely filled with sodium bicarbonate solids. The sodium bicarbonate container 102 can be filled only partially with water. As sodium bicarbonate concentrate is metered out of the sodium bicarbonate container 102 during use, additional fluid can be introduced into the sodium bicarbonate container 102, dissolving some of the remaining sodium bicarbonate solids at the bottom section 121 of the sodium bicarbonate container 102, so that the sodium bicarbonate solution remains approximately saturated.

Sodium chloride container 103 can be connected to fluid lines 107 and 109. Fluid line 107 can connect the sodium chloride container 103 to valve 113. Valve 113 can also connect to fluid line 112, which in turn connects to the main dialysate flow loop 106. Fluid line 109 can connect to valve 114, which also connects to fluid line 115 and the main dialysate flow loop 106. Pump 105 can control the movement of fluid through lines 115 and 109.

Sodium bicarbonate container 102 can be connected to fluid lines 110 and 108. Fluid line 108 can also connect to valve 113. Fluid line 110 can also connect to valve 114. Cation infusate container 101 can be connected by fluid line 111 to the main dialysate flow loop 106. Pump 104 can control the movement of fluid through line 111. Either or both of pumps 104 and 105 can be capable of moving fluid bi-directionally. That is, either one or both of the pumps can move fluid from the containers seat or received inside the infusate caddy to the main dialysate flow loop 106, or from the main dialysate flow loop 106 to any of the containers within the infusate caddy. Pump 104 can occlude line 111 and prevent flow in either direction between cation infusate container 101 and the main dialysate flow loop 106. Pump 105 can occlude line 115 and simultaneously prevent flow in either direction between the main dialysate flow loop 106 and both the sodium bicarbonate container 102 and sodium chloride container 103. Non-limiting examples of such pumps include positive displacement pumps such as roller-type peristaltic pumps and reciprocating piston pumps.

As shown in FIG. 2, the valves and pumps can be selectively opened and closed to form a priming flow path, for priming the sodium chloride container 103, listed as step 3 in FIG. 1. In FIG. 2, dotted lines denote fluid lines containing gas, while solid lines denote fluid lines containing liquid. The light colored portions of a valve denote the valve is open in those directions, while the dark colored portions denote the valve is closed in those directions. To prime the sodium chloride container 103, pump 105 can pump water from the main dialysate flow path 106 into line 115, as shown by arrow 116. Valve 114 can be used to direct the water through line 109 and into sodium chloride container 103, as shown by arrow 117. The water can fill the bottom section 119 of sodium chloride container 103 to dissolve a portion of the solid sodium chloride to produce an approximately saturated sodium chloride solution in the bottom section of sodium chloride container 103. Some air can be allowed to remain in the top section 118 of sodium chloride container 103. Sequestering air at the top section 118 of sodium chloride container 103 can prevent uncontrolled flow of sodium chloride solution from sodium chloride container 103 through line 107 to either the main dialysate flow loop 106 or sodium bicarbonate container 102. Any air that is displaced from sodium chloride container 103 during priming can flow through line 107 through valve 113 into line 112 and the main dialysate flow loop 106 where the air can be removed with a degasser. One skilled in the art will understand that additional soluate or materials can be included in caddy containers not shown in FIG. 2. For example, urease may be included for addition to a sorbent cartridge. Further, additional infusates, such as barium carbonate, may be added to control solute concentrations in the dailysate. Any number of additional containers can be primed in the same fashion as described for sodium bicarbonate container 102 or sodium chloride container 103.

Figure 3:
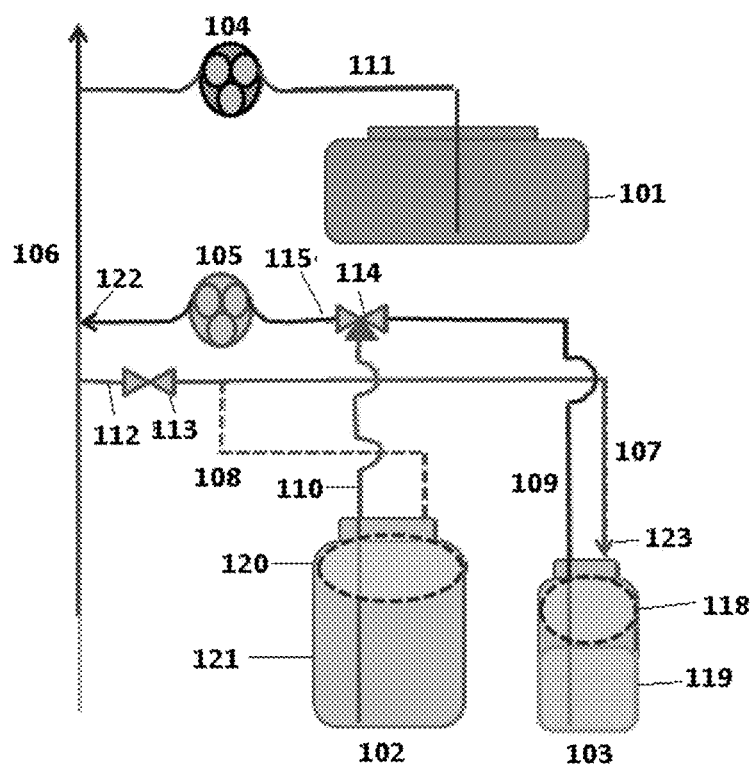
FIG. 3 shows a flow path of the connectors, pumps and valves in an infusate caddy using one two-way valve and one three-way valve controlling fluid to the sodium chloride and sodium bicarbonate containers.

FIG. 3 shows the pumps, valves and connections selectively opened and closed to form a dialysate flow path for metering of sodium chloride solution from sodium chloride container 103 into dialysate flow path 106, shown as step 4 in FIG. 1. The components in FIG. 3 are the same as the components in FIG. 2 wherein the same reference numbers in each of the figures refer to the same components. Pump 105 can be reversed, so that instead of pumping water from the dialysate flow path 106 into the sodium chloride container 103, the pump 105 instead pumps the sodium chloride solution from the sodium chloride container 103 into the dialysate flow path 106, as shown by arrow 122. Valve 114 can be configured to allow the sodium chloride solution to be pumped from the sodium chloride container 103 into the dialysate flow loop 106 by action of pump 105, while preventing any movement of fluid out of the sodium bicarbonate container 102 through line 110. As fluid is moved out of the sodium chloride container 103, valve 113 can be opened to allow fluid to move from the dialysate flow loop 106 into the sodium chloride container 103, as shown by arrow 123, keeping a relatively constant amount of fluid in both the dialysate flow loop and the containers within the caddy. Concentration sensors, such as conductivity sensors, can ensure that the fluid in the dialysate flow loop 106 has the desired sodium chloride concentration.

Figure 4:
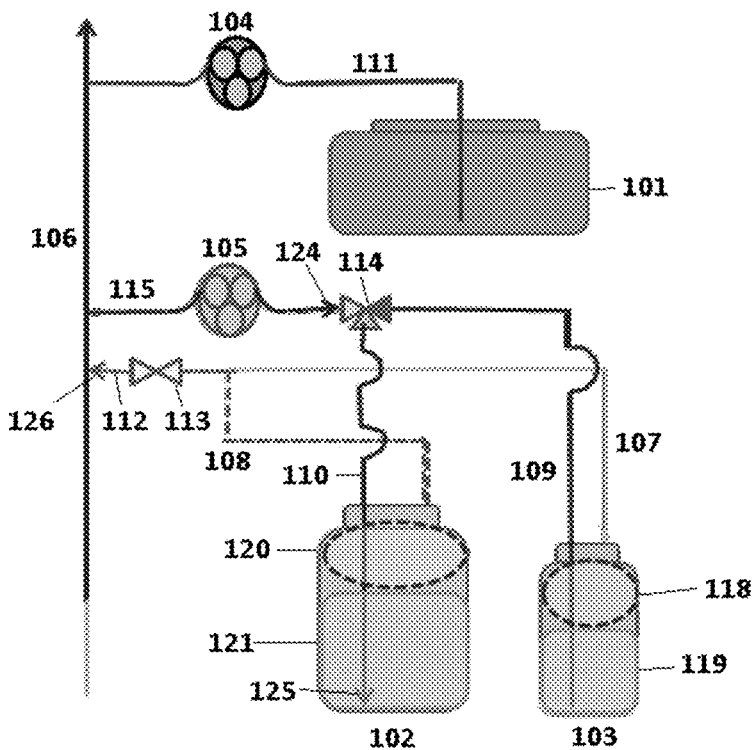
FIG. 4 shows a flow path of the connectors, pumps and valves in an infusate caddy using one two-way valve and one three-way valve controlling fluid to the sodium chloride and sodium bicarbonate containers.

FIG. 4 shows the same system where the pumps and valves are selectively opened and closed to form a priming flow path for priming of the sodium bicarbonate container 102, shown as step 5 in FIG. 1. Valve 114 can be selectively opened and closed to allow water from the dialysate flow loop 106 into the sodium bicarbonate container 102 by action of pump 105 through line 110 as represented by arrows 124 and 125, while preventing water from entering the sodium chloride container 103 through line 1109. The sodium bicarbonate container 102 can contain sodium bicarbonate solids. The water added to the sodium bicarbonate container 102 can dissolve the sodium bicarbonate to make an approximately saturated sodium bicarbonate solution in the bottom section 121 of the sodium bicarbonate container 102. Sodium bicarbonate container 102 can be partially filled such that a volume of air 120 can remain in the top section 120 of the sodium bicarbonate container 102. The air remaining in the top section 120 can prevent uncontrolled flow of sodium bicarbonate solution from flowing out of the sodium bicarbonate container 102 and the dialysate flow loop 106. As water is introduced to sodium bicarbonate container 102 through line 110, air can be displaced to the dialysate flow loop 106 through line 112 and valve 113, as represented by arrow 126 and the air can be removed by a degasser (not shown).

Figure 5:
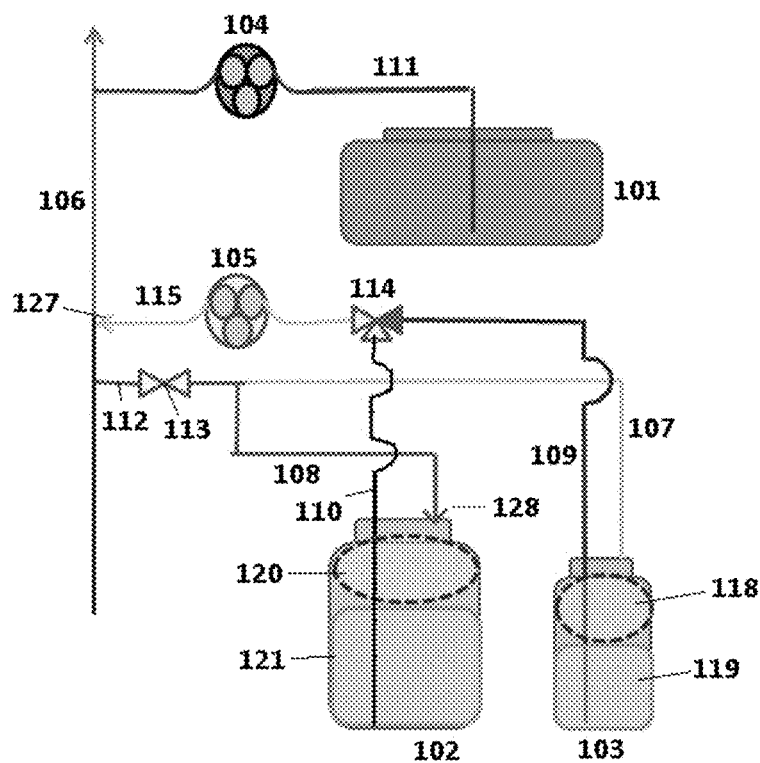
FIG. 5 shows a flow path of the connectors, pumps and valves in an infusate caddy using one two-way valve and one three-way valve controlling fluid to the sodium chloride and sodium bicarbonate containers.

FIG. 5 shows the same system with the pumps and valves selectively opened and closed to form a dialysate flow path for pumping the sodium bicarbonate solution from the sodium bicarbonate container 102 into the dialysate flow loop 106, listed as step 6 in FIG. 1 to generate a dialysis fluid with a concentration of solutes suitable for use in dialysis. Pump 105 can again be reversed, so pump 105 pumps fluid from the sodium bicarbonate container 102 into the dialysate flow loop 106. The sodium bicarbonate solution can travel through line 110, valve 114 and then line 115 as represented by arrow 127. Fluid from the dialysate flow loop 106 can move through line 112 and valve 113 into the sodium bicarbonate container 102, by line 108 as shown by arrow 128. The sodium bicarbonate solution can enter the dialysate flow loop 106, and combine with the sodium chloride solution moved previously to create a dialysate with a desired sodium chloride and sodium bicarbonate concentration. Concentration sensors, such as conductivity sensors or pH sensors, can ensure that the system has generated a dialysis fluid with a concentration of solutes suitable for use in dialysis in the dialysate flow loop 106. The concentration sensors can ensure that the concentration of sodium bicarbonate and sodium chloride in the generated dialysis fluid is within a range safe for use in dialysis.

Figure 6A:
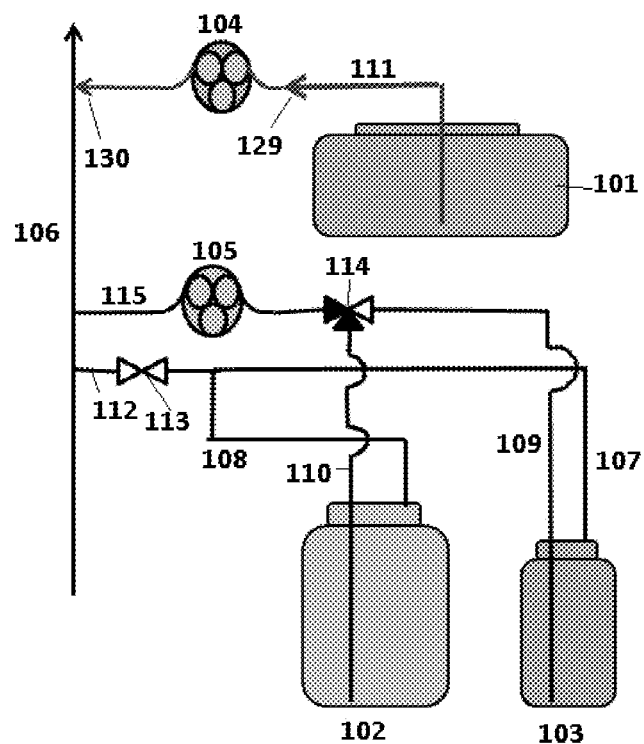
FIG. 6a shows a flow path of the connectors, pumps and valves in an infusate caddy using a two-way valve and a three-way valve controlling the clearing of disinfection solution from cation infusate lines.
Figure 6B:
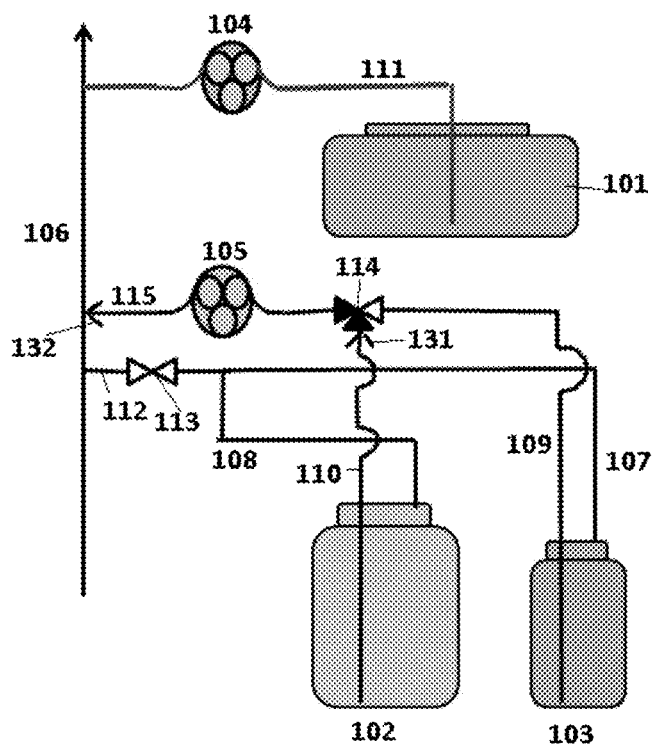
FIG. 6b a flow path of the connectors, pumps and valves in a infusate caddy using a two-way valve and a three-way valve controlling the clearing of disinfection solution from sodium bicarbonate lines.
Figure 6C:
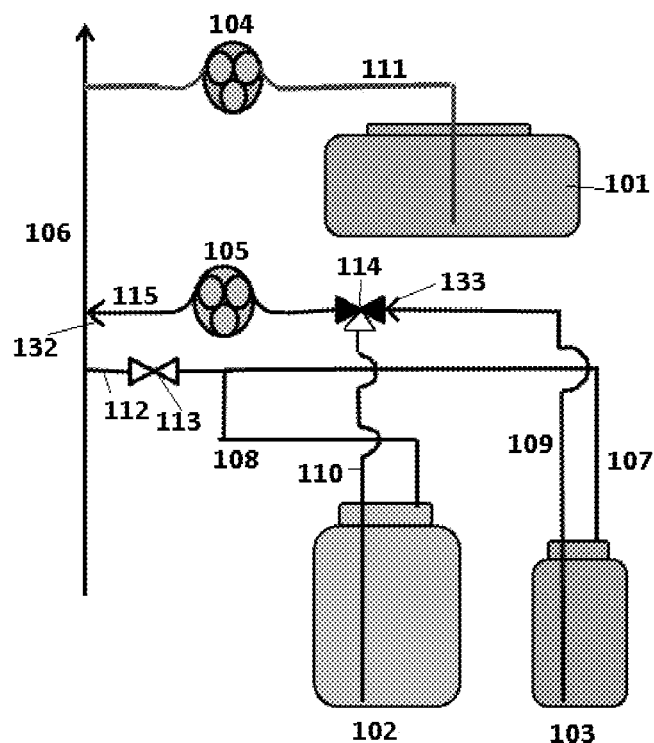
FIG. 6c a flow path of the connectors, pumps and valves in a infusate caddy using a two-way valve and a three-way valve controlling the clearing of disinfection solution from sodium chloride lines.

FIGS. 6a-c illustrate the steps necessary to clear the disinfection solution out of the lines connecting the containers seated in the infusate caddy to the dialysis system, described in step 2 of FIG. 1. FIG. 6a illustrates a disinfectant solution that can be pumped from line 111 and pump 104 into the main dialysate flow loop 106 before the cation infusate container 101 is primed. The step moves the disinfectant solution by action of pump 104 into the dialysate flow loop 106, as illustrated by arrows 129 and 130, where the disinfectant solution can be drained and flushed from the fluid pathways of the dialysis machine (not shown).

FIG. 6b illustrates a disinfectant solution pumped from line 110, line 115 and pump 105 into the main dialysate flow loop 106. The step moves the disinfectant solution by action of pump 105 into the dialysate flow loop 106 as shown by arrow 132, where disinfectant solution can be drained and flushed from the fluid pathways of the dialysis machine (not shown). During the step, air from the sodium bicarbonate container 102 can flow into the lines through valve 114, as shown by arrow 131.

FIG. 6c illustrates a disinfection solution being pumped from line 110, line 115 and pump 105 into the main dialysate flow loop 106. The step moves the disinfectant solution by action of pump 105 into the dialysate flow loop 106 as shown by arrow 132, where disinfectant solution can be drained and flushed from the fluid pathways of the dialysis machine (not shown). By selectively opening and closing valve 114, air from the sodium chloride container 103 can flow into the lines through valve 114, as shown by arrow 133.

Figure 6D:
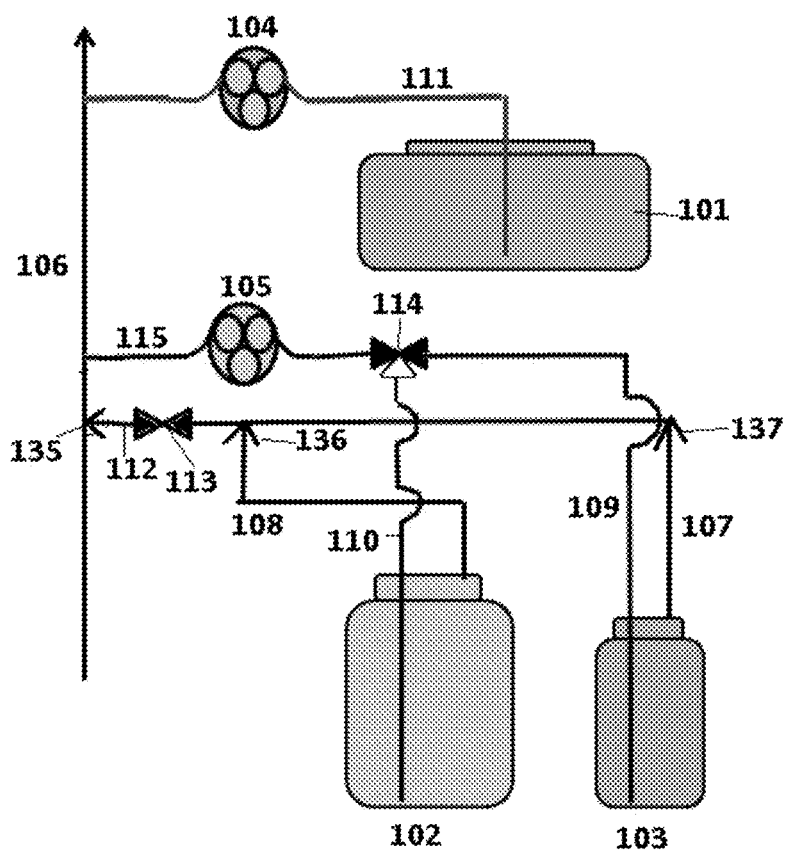
FIG. 6d a flow path of the connectors, pumps and valves in a infusate caddy using a two-way valve and a three-way valve controlling the clearing of disinfection solution from sodium chloride and sodium bicarbonate lines.

FIG. 6d shows a disinfectant solution pumped from line 108, line 107, valve 113 and line 112 into the main dialysate flow loop 106. To accomplish the step, a pump (not shown) is in fluid communication with the main dialysate flow loop line 106 and is operated to evacuate fluid from main dialysate flow loop line 106 to create a negative pressure in main dialysate flow loop line 106. After the negative pressure is created in main dialysate flow loop line 106, valve 113 is opened to allow the disinfectant to drain into the main dialysate flow loop line 106, as shown by arrow 135, from lines 107 and 108 as shown by arrows 137 and 136, where disinfectant solution can be drained and flushed from the fluid pathways of the dialysis machine (not shown).

During dialysis, valve 114 as shown in FIGS. 2-6 can be switched between the sodium chloride container 103 and sodium bicarbonate container 102 to selectively meter concentrated sodium chloride or sodium bicarbonate solution into the dialysate flow loop 106, generating a dialysis fluid with a concentration of sodium chloride and sodium bicarbonate suitable for use in dialysis. Pump 105 can be cleared of any concentrated solution when switching between sodium bicarbonate and sodium chloride addition. To clear the pump 105 of concentrated solution, the pump can be reversed to draw an amount of fluid from the dialysate flow loop 106 into the sodium chloride line 109 or sodium bicarbonate line 110. Drawing the fluid can wash the pump 105 of any concentrated solution left in the lines immediately adjacent to the pump 105. The valve 114 can then be switched to change the concentrate being added without adding any additional concentrate that may have been left in the lines. Pump 104 can be used during dialysis as necessary to add cation infusates or any other treatment solutes from the cation infusate container 101 into the dialysate flow loop 106 by line 111. The lines, valves and pumps can be of any type known in the art. The pumps can be positive displacement pumps that occlude the lines and prevent flow when the pumps are not operating, or the pumps can be centrifugal or gear pumps, and additional valves can be added to prevent unintended flow through the pump. The valves described as 2-way, 3-way or 4-way valves can be replaced with different valves or valve assemblies to accomplish the same functions.

The pumps and valves can be operated by an electronic control system. The electronic control system can be programmed to carry out the steps described in FIGS. 1-6. The control system can be programmed to move a predetermined amount of fluid into and out of the containers described, allowing the control system to control each of the solutes in the dialysate during a dialysis session.

Figure 7:
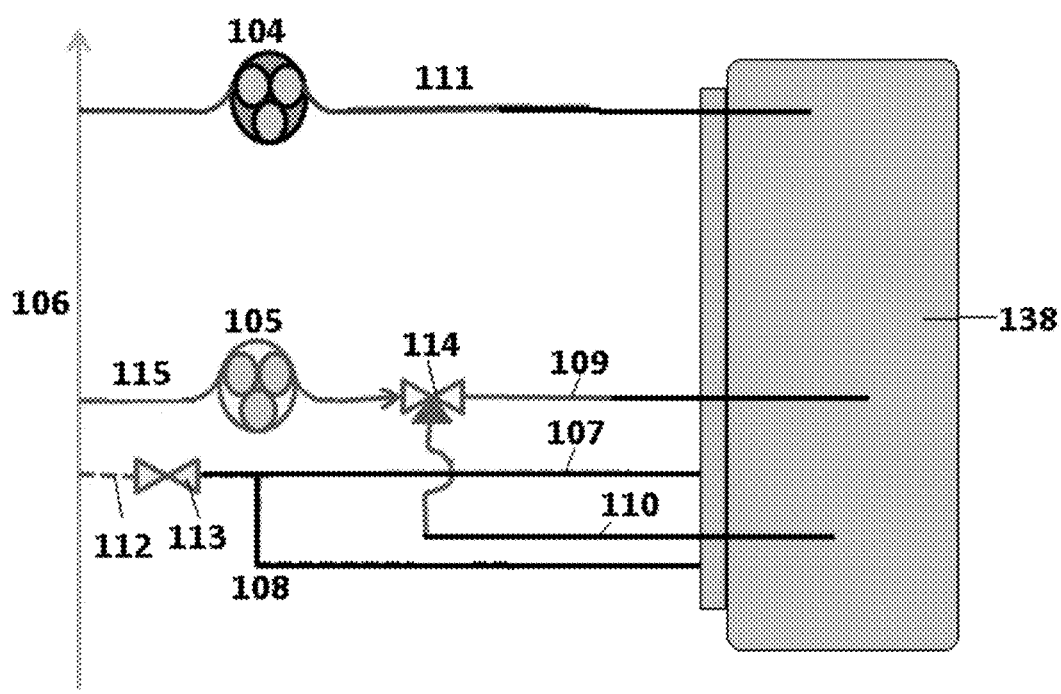
FIG. 7 shows a flow path of the connectors, pumps and valves in an infusate caddy configured for priming the system with disinfectant.
Figure 8:
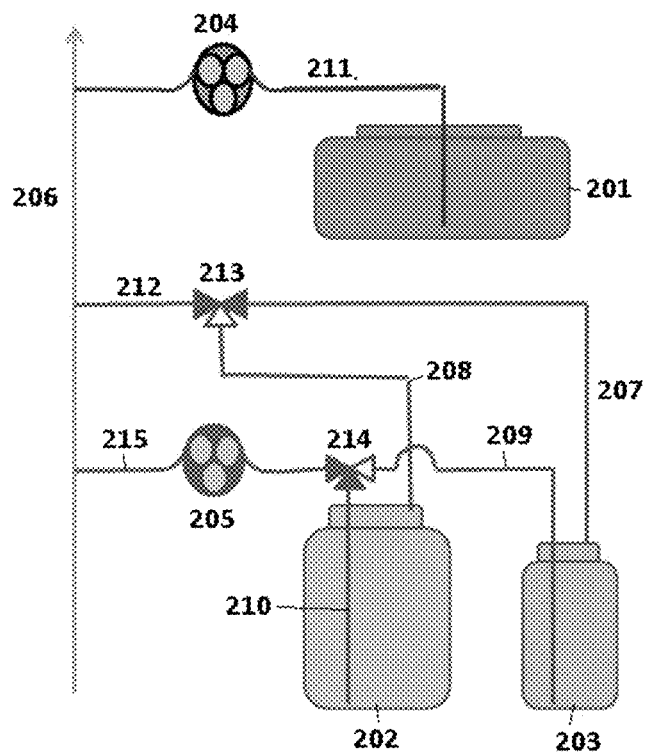
FIG. 8 shows a flow path of the connectors, pumps and valves in an infusate caddy using two three-way valves.

FIG. 7 shows a system configured to prime the system for disinfection. Components with the same reference numbers in FIG. 7 as in FIGS. 2-6 correspond to the same components. The system in FIG. 7 is one embodiment of the system in FIGS. 2-6, redrawn for simplicity. The infusate caddy can include a disinfection container 138 inside the caddy wherein the disinfection container 138 is connected to the infusate container connectors and dialysis machine connectors when the caddy is placed in a disinfection configuration. In FIG. 7, the fluid lines from the dialysis machine can be connected to disinfection container 138. Fluid line 111 and pump 104 can be used to flow disinfectant from the disinfectant container 138 into fluid line 111 and dialysate flow loop line 106 in order to prime the entire dialysis system with disinfectant. Similarly, pump 105 can be used to move disinfection solution from the disinfection container 138 into the dialysate flow loop line 106 through lines 107, 108, 109, and 110. Valves 114 and 113 can be switched as required to ensure that the disinfection solution reaches all fluid lines in the system. The disinfection solution can be recirculated through the disinfection container 138 and the dialysis system. One skilled in the art will understand that other arrangements of the pumps, valves and connectors are possible beyond that which is shown in FIGS. 2-7. FIG. 8 shows an arrangement utilizing two three-way valves 213 and 214. In FIG. 8, line 206 can represent the main operational dialysate flow loop. Cation infusate container 201, sodium bicarbonate container 202 and sodium chloride container 203 can be placed in an infusate caddy, and the infusate caddy seated in a receiving compartment on a top portion of a dialysis machine. Fluid connectors for fluidly connecting flow between the infusate containers and line 206 can be connected. The cation infusate container 201 can be fluidly connected to line 211, which allows fluid to move between the cation infusate container 201 and the dialysate flow loop 206. Adding fluid from the cation infusate container 201 to the dialysate flow loop 206 can be controlled by cation infusate pump 204. Sodium chloride container 203 can be fluidly connected to line 207, which allows fluid or gas to enter the sodium chloride container 203. The sodium chloride container 203 can also be fluidly connected to line 209, which allows fluid or gas to leave the sodium chloride container 203 and enter the rest of the dialysis system through dialysate flow loop line 206. Sodium bicarbonate container 202 can be connected to line 208, which allows fluid or gas to enter the sodium bicarbonate container 202, and also can be fluidly connected to line 210, which allows fluid or gas to leave the sodium bicarbonate container 202 and enter the dialysate flow loop through dialysate flow loop line 206. The movement of fluid or gas from dialysate flow loop 206 into the sodium chloride container 203 or sodium bicarbonate container 202 can be controlled by valve 213. Valve 213 can control the movement of fluid or gas from line 212, fluidly connected to dialysate flow loop line 206, into lines 207 and 208, controlling the movement of fluid or gas into the containers. The flow of fluid from the sodium chloride container 203 or sodium bicarbonate container 202 can be controlled by valve 214. Valve 214 can allow or prevent fluid from moving from lines 210 and 209 into line 215, which connects to dialysate flow loop line 206. Bicarbonate pump 205 can draw fluid from the sodium chloride container 203 or sodium bicarbonate container 202 into dialysate flow loop line 206, and to the rest of the dialysis system. Bicarbonate pump 205 can be a bi-directional pump, capable of moving fluid from line 215 into dialysate flow loop line 206, or from dialysate flow loop line 206 into line 215. Alternatively, multiple pumps can be utilized that can move fluid in opposite directions as opposed to a single pump capable of moving fluid in two different directions. The valves and pumps shown in FIG. 6 can be located inside of the caddy, or with the rest of the dialysis system outside of the caddy.

The steps depicted in FIG. 1 can be carried out with the configuration shown in FIG. 8 in the same manner as described in FIGS. 2-7. The pumps and valves can be selectively opened and closed to form a priming flow path, and water added from the dialysate flow loop 206 to the sodium chloride container 203 by drawing water from the dialysate flow loop 206, through fluid line 215 with pump 205. Valve 214 can be controlled to direct the water into sodium chloride container 203, while preventing fluid from entering sodium bicarbonate container 202. Air initially present in sodium chloride container 203 can leave through line 207, through valve 213 and into the dialysate flow loop 206 via line 212, where the air can be removed from the dialysate flow loop 206 with a degasser. Sodium chloride solution can then be pumped to the dialysate flow loop 206 by switching the direction of pump 205 to move fluid from the sodium chloride container 203 into the dialysate flow loop 206.

The sodium bicarbonate container 202 can be primed by switching valve 214 to pump water from the dialysate flow loop 206 into the sodium bicarbonate container 202 via line 210. Air initially present in the sodium bicarbonate container 202 can leave through line 208. Sodium bicarbonate solution can then be pumped to the dialysate flow loop 206 by switching the direction of pump 205 to pump fluid from the sodium bicarbonate container 202 to the dialysate flow loop 206 through lines 210 and 215. The addition of the sodium chloride and sodium bicarbonate to the dialysate flow loop 206 generates a dialysis fluid with a concentration of solutes suitable for use in dialysis.

Figure 9A:
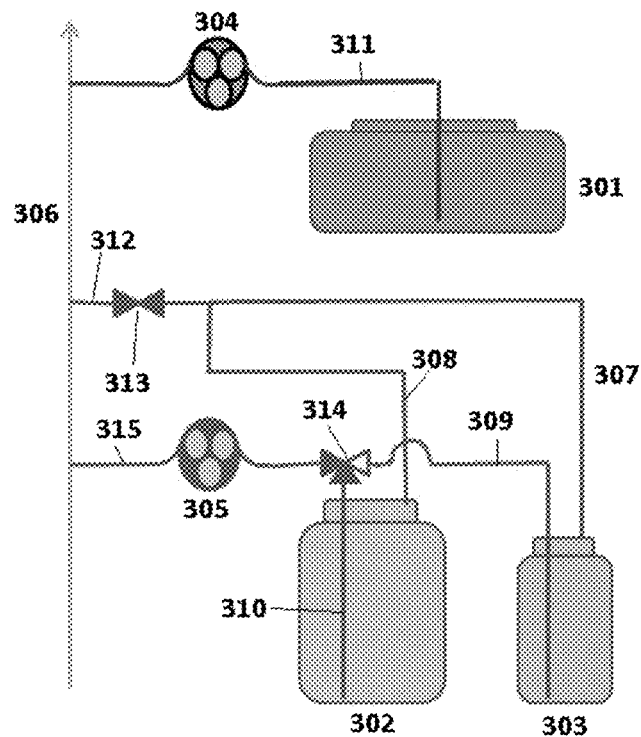
FIG. 9a shows a flow path of the connectors, pumps and valves in an infusate caddy using one two-way valve and one three-way valve.
Figure 9B:
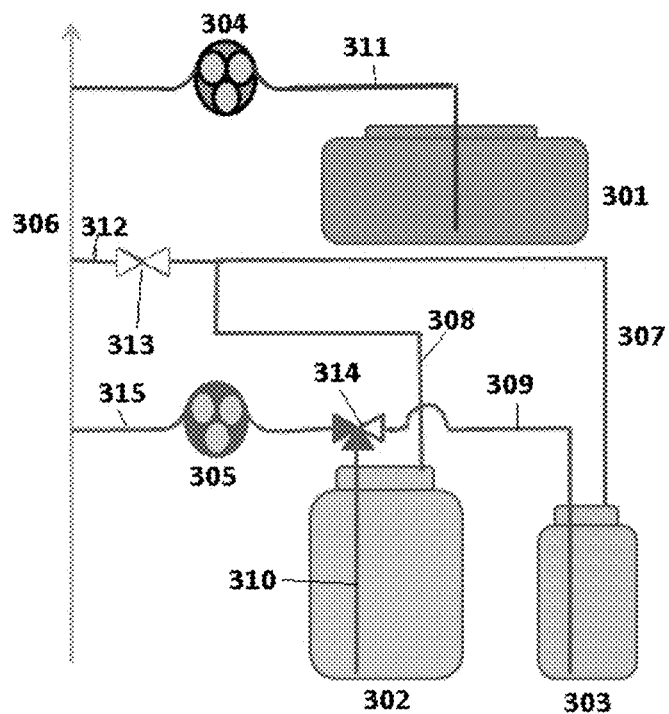
FIG. 9b shows a dialysate flow path of the connectors, pumps and valves in an infusate caddy configured for flushing and filling the dialysis system.

FIGS. 9a and 9b show a flow diagram for infusate containers seated in an infusate caddy fluidly connected to a dialysate flow path utilizing a two-way and a three-way valve. Cation infusate container 301 can be fluidly connected to cation infusate line 311. Cation infusate pump 304 can control the movement of fluid from cation infusate container 301, through cation infusate line 311 into the dialysate flow loop line 306. Cation infusate pump 304 can be a positive displacement pump, such as a peristaltic pump that occludes line 311 and prevents liquid from flowing uncontrolled from dialysate flow loop line 306 into cation infusate container 301. Sodium chloride container 303 can be fluidly connected to line 307, which can allow fluid or gas to move between dialysate flow loop line 306 and the sodium chloride container 303. Sodium chloride container 303 can also be fluidly connected to line 309, allowing fluid from the sodium chloride container 303 into the rest of the dialysate flow loop 306 through valve 314 and pump 305. Sodium bicarbonate container 302 can be fluidly connected to line 308, allowing fluid and gas to move between the sodium bicarbonate container and dialysate flow loop line 306. Sodium bicarbonate container 302 can also be fluidly connected to line 310, allowing fluid or gas to move between the sodium bicarbonate container 302 and dialysate flow loop line 306 through valve 314 and pump 305. Two-way valve 313 can be selectively opened and closed to control the movement of fluid or gas between dialysate flow loop line 306 and the sodium chloride container 303 and sodium bicarbonate container 302. Three-way valve 314 can control the movement of fluid and gas between either the sodium chloride container 303 or sodium bicarbonate container 302 and the dialysate flow loop line 306 via line 315. Pump 305 can provide the driving force necessary to move fluids or gas to or from the sodium chloride container 303 or sodium bicarbonate container 302 to dialysate flow loop line 306. Pump 305 can be a positive displacement pump, such as a peristaltic pump that occludes line 315 and prevents liquid from flowing uncontrolled from dialysate line 306 into sodium bicarbonate container 302 or sodium chloride container 303. Pump 305 can be a bi-directional pump, capable of moving fluids and gas in either direction through line 315.

In FIG. 9a, the valves 313 and 314 can be selectively opened and closed to form a priming flow path. The valves 313 and 314 are shown as open to flow lines where the valve portion is filled, and closed to flow lines where the valve portion is unfilled. Valve 313 is shown open to the dialysate flow loop line 306 and valve 314 is shown in a state that directs flow to occur only between pump 305 and sodium bicarbonate container 302 and prevents flow between pump 305 and sodium chloride container 303. Because valve 313 is open, fluids and gas can pass between dialysate flow loop line 306 and either the sodium bicarbonate container 302 or sodium chloride container 303.

The steps described in FIG. 1 can be carried out with the configuration shown in FIGS. 9a and 9b in the same manner. The sodium chloride container 303 can be filled with water from the dialysate flow loop 306 by using pump 305 to draw water in to line 315. Valve 314 can be selectively opened and closed to form a priming flow path and allow water from line 315 to enter the sodium chloride container 303 through line 309. Air originally present in sodium chloride container 303 can leave through line 307, through valve 313 and line 312, into the dialysate flow loop 306, where the air can be removed by a degasser. The dialysate flow loop can be primed with sodium chloride by selectively opening and closing the pumps and the valves to form a dialysate flow path, and switching pump 305 to move fluid from sodium chloride container 303, through line 309 and into the dialysate flow loop 306 via line 315.

The sodium bicarbonate container 302 can be filled with water from the dialysate flow loop 306 by selectively opening and closing valve 314 and pump 305 to form a priming flow path and draw water from the dialysate flow loop 306 through line 315 and into the sodium bicarbonate container 302 by line 310. Air present in the sodium bicarbonate container 302 can leave through line 308, through valve 313 and line 312, into the dialysate flow loop 306, where the air can be removed by a degasser. The sodium bicarbonate can be added to the dialysate flow loop 306 by selectively opening and closing the valves and switching pump 305 to move fluid from sodium chloride container 303, through line 309 and into the dialysate flow loop 306 via line 315. If necessary, pump 304 can be used to draw water into the cation infusate container 301 through line 311, and then during dialysis the pump 304 can be switched to move infusate solution from the cation infusate container 301 into the dialysate flow loop 306.

As shown in FIG. 9b, after the caddy is attached to the dialysis system, the system can be flushed of any fluid, filled with water, and then primed. The valve configuration shown in FIG. 9b can be used during flushing and filling the dialysis system. If pump 305 occludes line 315 and by keeping valve 313 closed to the dialysate flow loop line 306 during flushing and filling, no citric acid or other disinfectants can enter the sodium chloride container 303 or sodium bicarbonate container 302.

The valves connecting the dialysate flow loop to the infusate containers seated in the infusate caddy as described in FIGS. 2-9 can be closed to the dialysate flow loop, such that fluid cannot move from the dialysate flow loop into the sodium bicarbonate, sodium chloride or cation infusate containers keeping citric acid or other disinfectants originally present in the dialysate flow loop from contaminating the sodium chloride or sodium bicarbonate solutions.

Figure 14:
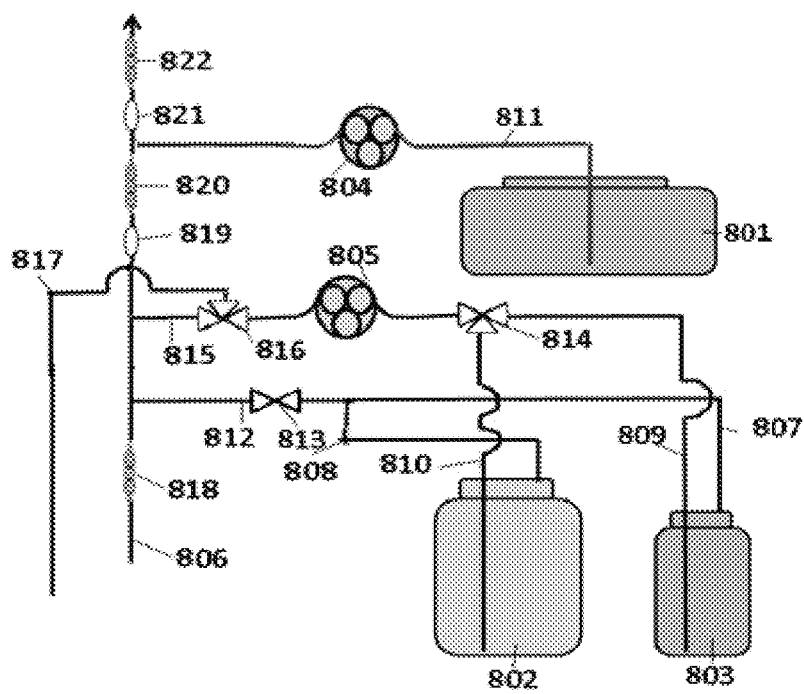
FIG. 14 shows a flow path diagram with a two-way valve and two three-way valves.

FIG. 14 illustrates a flow diagram for infusate containers seated in an infusate caddy fluidly connected to a dialysate flow path utilizing an additional three-way valve 816. The infusate caddy can contain a cation infusate container 801, a sodium bicarbonate container 802, and a sodium chloride container 803, each of which can contain a solid source or a concentrate. Sodium chloride container 803 can be connected to fluid lines 807 and 809. Fluid line 807 can connect the sodium chloride container 803 to valve 813. Valve 813 can also connect to fluid line 812, which in turn connects to the main dialysate flow path 806 allowing fluid from the dialysate flow path 806 to enter the sodium chloride container 803. Fluid line 809 can connect to valve 814, which also connects to valve 816 downstream of pump 805. Pump 805 can control the movement of fluid through line 809 and valve 816. Valve 816 can be operated to direct fluid into the main dialysate flow path 806 during treatment by fluid line 815, or alternatively to direct fluid through fluid line 817 to a separate portion of the dialysate flow path 806. As described, directing sodium chloride and sodium bicarbonate upstream of a sorbent cartridge (not shown in FIG. 14) can reduce the time necessary for priming the dialysis machine. Valve 816 allows the sodium chlroide and sodium bicarbonate to be pumped either upstream or downstream of the sorbent cartridge during priming and treatment, respectively.

Sodium bicarbonate container 802 can be connected to fluid lines 810 and 808. Fluid line 808 can also connect to valve 813 and can allow fluid from the dialysate flow path 806 to enter the sodium bicarbonate container 802. Fluid line 810 can also connect to valve 814. Cation infusate container 801 can be connected by fluid line 811 to the main dialysate flow path 806. Pump 804 can control the movement of fluid through line 811.

Either or both of pumps 804 and 805 can be capable of moving fluid bi-directionally to move fluid from the containers within the infusate caddy to the main dialysate flow loop 806, or from the main dialysate flow loop 806 to any of the containers within the infusate caddy.

During treatment, various sensors can determine the concentration of sodium chloride, sodium bicarbonate, and cations added to the dialysate flow path 806 from the caddy containers. Conductivity sensor 818 can determine the conductivity of the dialysate prior to addition of sodium bicarbonate, sodium chloride, or other cations. Based on the conductivity detected by conductivity sensor 818, the amount of each fluid that needs to be added to the dialysate can be determined. Conductivity sensor 820, located downstream of fluid line 815, can determine the conductivity of the dialysate after addition of sodium bicarbonate, and ensures that the correct amount of sodium bicarbonate is added to the dialysate. Static mixer 819 can ensure complete mixing of the added sodium bicarbonate and the dialysate for accurate measurements by conductivity sensor 820. Conductivity sensor 822, located downstream of fluid line 811, can determine the conductivity of the dialysate after addition of the cation infusates, and ensure that the correct amount the cations is added to the dialysate. Conductivity sensor 822 can also provide a final check of the dialysate conductivity prior to the dialysate entering the dialyzer (not shown in FIG. 14). If the detected conductivity is outside of a predetermined range, the system can provide an alert, shutdown, or bypass the dialyzer to avoid delivering an unsafe dialysate to the patient. Static mixer 821 can ensure complete mixing of the added cation infusates and the dialysate for accurate measurements by conductivity sensor 822. The static mixers and sensors illustrated in FIG. 14 can be included in any of the described caddy configurations.

Figure 15:
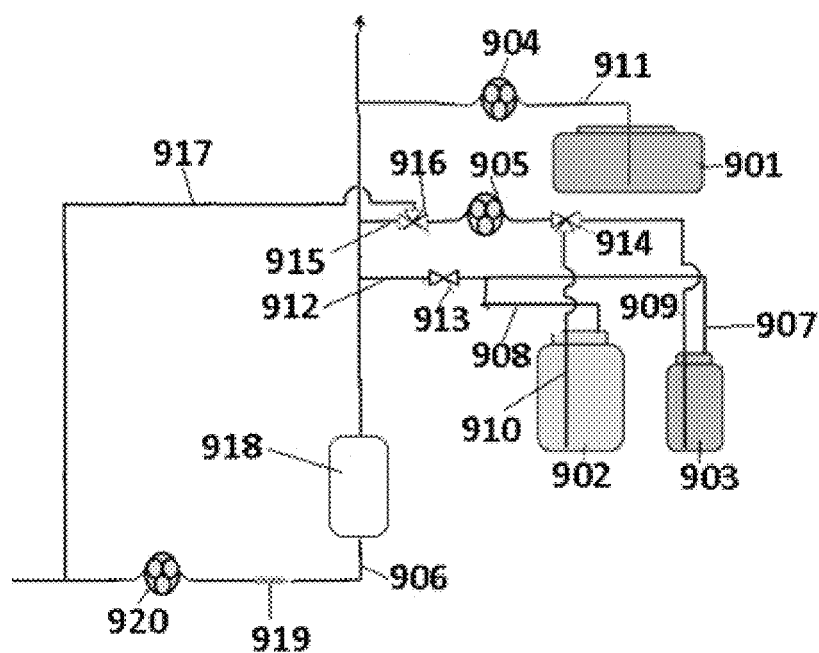
FIG. 15 shows a portion of a dialysate flow path connected to infusate containers in a caddy.

FIG. 15 illustrates a simplified portion of a dialysate flow path 906 using the infusate caddy flow diagram. Sodium chloride container 903 can be connected to fluid lines 907 and 909. Fluid line 907 can connect the sodium chloride container 903 to valve 913. Valve 913 can also connect to fluid line 912, which in turn connects to the main dialysate flow path 906 allowing water from the dialysate flow path 906 to enter the sodium chloride container 903 for priming of the sodium chloride container 903. Fluid line 909 can connect to valve 914, which also connects to valve 916 downstream of pump 905. Pump 905 can control the movement of fluid through line 909 and valve 916. Valve 916 can be selectively openend and closed to direct fluid into the main dialysate flow path 906 during treatment by fluid line 915, or alternatively to direct fluid through fluid line 917 to a separate portion of the dialysate flow path 906.

Sodium bicarbonate container 902 can be connected to fluid lines 910 and 908. Fluid line 908 can also connect to valve 913 and can allow water from the dialysate flow path 906 to enter the sodium bicarbonate container 902. Fluid line 910 can also connect to valve 914. Cation infusate container 901 can be connected by fluid line 911 to the main dialysate flow path 906. Pump 904 can control the movement of fluid through line 911.

As described, valve 916 allows fluid to be directed to the dialysate flow path 906 upstream of sorbent cartridge 918. To reuse a dialyzer (not shown in FIG. 15), the dialyzer can be sterilized with a disinfectant solution. The disinfectant solution must then be flushed out of the dialyzer and dialysate flow path 906 by pumping fluid through the dialysate flow path 906. The sorbent cartridge 918 must then be flushed, drained, conditioned with sodium bicarbonate and primed with sodium chloride. Without valve 916, sorbent cartridge 918 can fill with water prior to conditioning. The sorbent cartridge 918 can then be flushed with additional sodium bicarbonate solution that has passed through the entire dialysate flow path 906 for conditioning. By directing the sodium bicarbonte through fluid line 917 upstream of the sorbent cartridge 918, only fluid with sodium bicarbonate enters the sorbent cartridge 918, reducing the time necessary for conditioning of the sorbent cartridge 918. After conditioning, the sorbent cartridge 918 is primed with a sodium chloride solution. By directing the sodium chloride through fluid line 917 upstream of the sorbent cartridge 918, only fluid with sodium sodium chloride enters the sorbent cartridge 918, reducing the time necessary for priming of the sorbnet cartridge 918. The total time for conditioning and priming the system can be reduced by as much as 5-15 minutes by directing fluid upstream of the sorbent cartridge with valve 916. Pump 920 provides the driving force for conveying dialysate and priming solution through the dialysate flow path 906. Conductivity sensor 919 detects the conductivity of the fluid prior to entering the sorbent cartridge 918. The conductivity of the fluid, along with the flow rate of the fluid, can be used determine an amount of bicarbonate and sodium chloride pumped through the dialysate flow path 906, allowing closed loop control during priming and flushing. One of skill in the art will understand a valve similar in function to valve 916 can be included in any of the described caddy configurations.

Infusate Caddy

Figure 10:
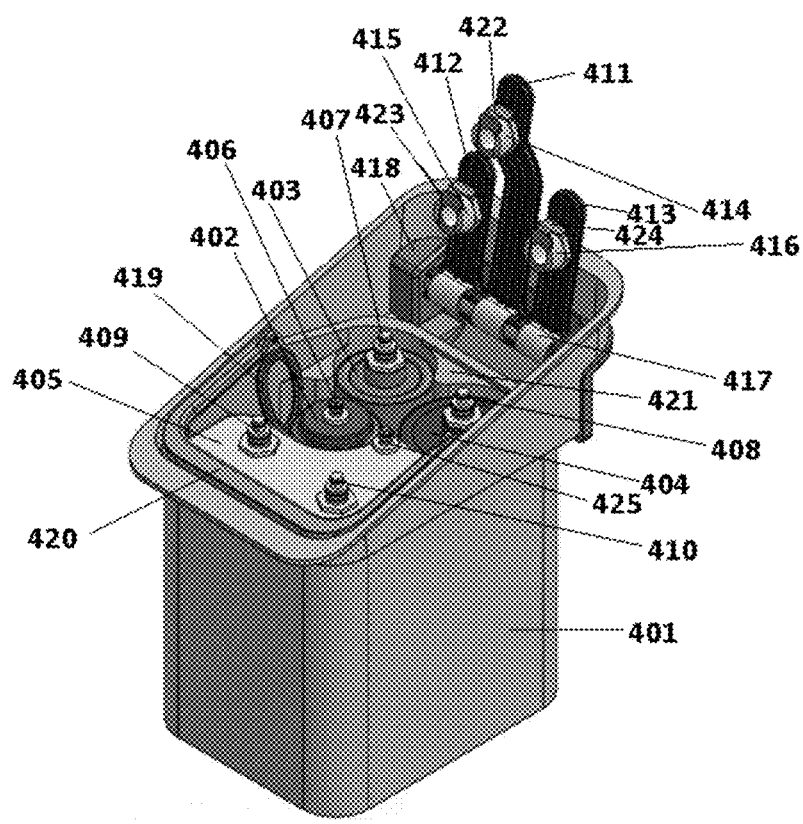
FIG. 10 shows an infusate caddy containing solute containers seated in a receiving compartment of a dialysis machine.

In FIG. 10, the infusate caddy 421 can be placed in a receiving compartment 401 positioned on a top console portion of a dialysis machine. The infusate caddy 421 can be configured to contain one or more receiving compartments in which infusate containers that contain the ion sources, infusates, electrolytes, other solutes, or combinations thereof, needed for dialysis, can be seated or positioned. The infusate caddy 421 can have a fitting feature inside the receiving compartment such as a protrusion, indentation, groove, or ridge positioned wherein the fitting feature has any shape, size, or geometry that is complementary to a corresponding fitting feature on the infusate containers. For example, the fitting feature can be positioned on an interior surface of the receiving compartment of the caddy 421, wherein the receiving compartment is designed to receive an infusate container designed to occupy a unique position inside the caddy 421. In one-non-limiting example, a curved wedge protrusion 424 and a curved wedge protrusion 425 are positioned on the walls of the receiving compartment of the infusate caddy 421. The respective radii of the cation infusate container 402 and the sodium bicarbonate container 403 can be sized to be positioned appurtenant to curved wedge protrusion 424. Similarly, the respective radii of sodium bicarbonate container 403 and sodium chloride container 404 can be sized to be positioned appurtenant to curved wedge protrusion 425. Each of the infusate containers can have unique shape and/or size to ensure that the infusate container is not inadvertently placed in the wrong receiving compartment of the infusate caddy 421. Optionally, a corresponding fitting feature can be positioned on a surface of the infusate container to ensure that the infusate container correctly mates or connects to the infusate caddy 421 at a unique position when placed inside the receiving compartment of the caddy 421.

The fitting feature is not limited to protrusions, indentations, grooves, or ridges, and can include any size and/or shape of the receiving compartment. For example, a depth, incline, or diameter of the receiving compartment of the caddy 421, can serve as a fitting feature and serve as a complementary surface. In such a case, the corresponding fitting feature can be an exterior surface shape, diameter, length, or curvature of an infusate container designed to fit inside the infusate caddy 421. Similarly, an exterior surface of the infusate caddy 421 itself, can have fitting features complementary to the receiving compartment 401 on the top portion of the dialysis machine 401. Similar to the receiving compartments of the infusate caddy 421, the receiving compartment 401 of the dialysis machine, can also have a specified fitting feature positioned on an interior surface as a curved wedge protrusion.

The ion sources and infusates sources can include cation infusate container 402, sodium bicarbonate container 403 and sodium chloride container 404. One skilled in the art will understand that the caddy 421 can be configured to contain any number of different combinations, shapes, and sizes of infusate containers in addition to those shown in FIG. 10. The fitting feature can include a visual indicator of the position of each of the containers, such as by labeling or color coding to indicate the correct position of each of the containers. For example, a label or color code can be affixed to indicate the correct position of each of the containers. The correct position of the sodium bicarbonate container receiving compartment can be colored blue, and the corresponding sodium bicarbonate container can also be colored blue. The correct position for the cation infusate container can be red, and the cation infusate container can also be red. The user can simply match the blue container to the blue position in the caddy, and the red container to the red position in the caddy. One of skill in the art will understand that any color or visual coding system including letters and symbols can be used to indicate the correct position for each container. The fitting feature can also be non-mechanical means for ensuring complementary connection such as magnets placed at particular locations in the infusate caddy 421. The caddy 421 can include fitting features that ensure specific containers can only occupy specific positions within the caddy 421. Further, the caddy 421 can contain more or less than four containers. Any combination of fitting features can be used together. For example, an infusate container can have a color code, a magnet of proper polarity, and a groove for proper mating to a corresponding receiving compartment in the infusate caddy 421. The caddy 421 can have a handle for easy removal of the container, such as handle 419.

Multiple infusate sources can be used in the caddy with other ions necessary for a dialysis session. The solute containers can contain an enzyme, such as urease, for addition to a sorbent cartridge, and other solutes for removal or control over concentrations of solutes in the dialysate, such as barium carbonate for control over sulfate in the dialysate. Any number of containers can be connected to any number of connectors. Each infusate can be in a separate container, such as a magnesium infusate container, a potassium infusate container and a calcium infusate container. Additionally, any of the containers shown in the figures can be avoided in the caddy 421.

Each of the containers can include a fluid connector for fluid connection to the dialysis system, such as connector

406 on cation infusate container 402, connector 407 on sodium bicarbonate container 403 or connector 408 on sodium chloride container 404. The fluid connectors may have affixed thereon, or may itself, be a fitting feature, as described herein, such that the fluid connectors can connect to a particular infusate container having a corresponding fitting for placement of the infusate container into the caddy 421 at the appropriate location. One or more valves (not shown in FIG. 10) can be included on the connectors to control the movement of fluid from the containers, through the connectors and into the dialysis system. One or more valves may also be included on connectors in the dialysis system fluidly connected to the connectors 406, 407, and 408 in order to control the movement of fluid from the containers through the connectors and into the dialysis system. Check valves (not shown) or a poppet type valve can be included on connectors 406, 407, and 408 to limit direction of flow to be unidirectional, or to prevent spillage when the connectors are disengaged. The valves may be 2-way, 3-way, 4-way or any other type of valve. The valves may be configured such that fluid can move through the connectors bi-directionally, that is, fluid may move from the containers into the dialysis system, or fluid may move from the dialysis system and into the containers. The connectors can be configured so both gas and liquid may move through the valves and into or out of the containers.

Any of the connectors can be coaxial connectors. Coaxial connectors allow simultaneous fluid ingress and fluid egress from the container through a single connector. Using coaxial connectors allows solid solute sources to be used in each of the containers because fluid can be directed into the containers to dissolve the solid solute, creating a solute solution, and then the solute solution can be added into the dialysis circuit. Using coaxial connectors also allows pressure equalization in the containers as fluid is added or removed, because gas can also be added or removed from the container at the same time.

The caddy 421 can also include a disinfection container, such as citric acid container 405. After dialysis is complete, the user can disconnect or remove sodium chloride container 404, sodium bicarbonate container 403, and cation infusate container 402, and connect the dialysis machine to citric acid container 405 through connectors 409 and 410. Citric acid can be moved from the citric acid container 405 into the fluid lines of the dialysis system to disinfect the system and prepare the system for the next use. The caddy 421 can be moved into a disinfection configuration as described in order to place citric acid container 405 in position for connection to the dialysis machine. Any of the containers can contain a solid material that can be dissolved to create the appropriate solution, such as solid sodium chloride in sodium chloride container 404. Water may be added to the sodium chloride container 404 through connector 408 during the priming and set up of the dialysis system. Because the sodium container 404 contains an amount of sodium chloride solids, when an amount of water is added to sodium chloride container 404, the resulting sodium chloride solution produced in sodium chloride container 404 will be approximately saturated and thus of a known concentration. The sodium chloride solution can then be used during dialysis. Similarly, the sodium bicarbonate container 403 can contain sodium bicarbonate solids and the cation infusate container 402 can contain a solid source of cations of a known mass, each of which can be dissolved with a known amount of water to create a fluid for dialysis. The cations can be present in cation infusate container 402 as a pre-mixed liquid which can be used in dialysis without additional water being added to cation infusate container 402 by the system.

The caddy 421 can include caddy connectors for connection to the connectors on each of the containers in the caddy. As shown in FIG. 10, the caddy connectors can be included on paddles 411, 412, and 413. The caddy connectors can connect to dialysis machine connectors for addition of the solute solutions into the dialysis system. The caddy 421 may include components for securing each of the containers in the proper location within the caddy 421 for proper connection to the dialysis machine. Furthermore, an exterior surface of the caddy connectors can have a fitting feature to ensure proper mating to corresponding infusate container. For example, a first caddy connector can have a hexagonal-shape while a second caddy connector can have a circular-shape. The corresponding infusate containers can have surfaces matched to receive the hexagonal- or circular shaped caddy connectors. One skilled in the art will understand that additional solute containers can be included in the caddy, and that additional paddles and connectors can be included as necessary.

The caddy connectors need not be included on paddles, and can be a length of hose, wherein the hose is fluidly connected to a dialysate flow path. The hose can be made of any material known in the art for use in dialysis systems, including silicone, reinforced silicone, or PVC. One skilled in the art will understand that other biocompatible materials can be used for the hose, and the hose is not limited to these materials. The hoses can be either flexible or semi-rigid, which would allow the hoses to move for connection to the containers in the caddy. The hoses can be sized and positioned such that each hose will only be able to connect with a single container within the caddy. For example, each hose may be positioned on a specific location with respect to the caddy, and each hose can be short enough so that the hose cannot reach any container not aligned with the specific location.

In FIG. 10, the locking means can be a paddle assembly 418. Each of the paddles 411, 412 and 413 in paddle assembly 418 can include a locking connector, such as caddy connector 414 on paddle 411, caddy connector 415 on paddle 412 and caddy connector 416 on paddle 413. After the infusate containers are properly placed inside the caddy 421, the paddles of the assembly 418 can be lowered and connected to corresponding container connectors 406, 407, and 408 on the containers within the caddy 421. The configuration of assembly 418 and caddy 421 can ensure that the correct connectors will be aligned to the correct container to prevent connection errors by the user. The paddles of the paddle assembly 418 can be lowered by pivoting the paddles on hinge 417. The caddy connectors 414, 415, and 416 can fit over the container connectors 406, 407, and 408, respectively. The caddy connectors 414, 415, and 416 can be tightened to lock the containers in place by twisting the caddy connectors 414, 415, and 416. Once tightened, the caddy connectors 414, 415, and 416 can lock the containers in place and resist inadvertent disconnection. The paddle assembly 418 can include a locking mechanism (not shown), so that after the paddles are lowered and locked into place, the paddles will resist inadvertent movement in a vertical and/or lateral direction. Further, the caddy connectors can include a locking mechanism 422 as shown on caddy connector 414, locking mechanism 423 as shown on caddy connector 415 and locking mechanism 424 as shown on caddy connector 416, each of which can lock the paddles on to the container connectors 406, 407, and 408.

The paddle assembly 418 may be constructed as part of a dialysis machine and positioned in a top section of the dialysis machine 401. The paddle assembly 418 can be constructed such that when the infusate caddy is placed within a receiving compartment on the dialysis machine, the paddles 411, 412, and 413 can be aligned to the respective containers for connection to the caddy connectors 414, 415, and 416. When the caddy 421 is placed into the receiving compartment 401, the paddles 411, 412, and 413 will align with each of the container connectors. By placing the paddle assembly 418 on the dialysis machine 401, the containers can be arranged within the caddy so that when the caddy is rotated, citric acid container 405 is aligned with one or more paddles 411 for connection to the dialysis machine 401. By rotating the caddy 421 so the citric acid container 405 is aligned for connection to the dialysis machine 401, the caddy 421 can be placed in a disinfection configuration, allowing citric acid to be moved from the citric acid container 405 through the container connectors 409, 410, and 425, and the caddy connectors 414, 415, and 416 on paddles 411, 412, and 413, and into the dialysis machine 401 for disinfection. The caddy 421 can include handle 420 for easy movement of the caddy 421. Citric acid container 405 can contain internal fluid pathways between any of connectors 409, 410, and 425 to allow a cleaning and/or disinfection solution to be recirculated through one or more of connectors 414, 415 and 416 by action of a single pump.

Figure 11:
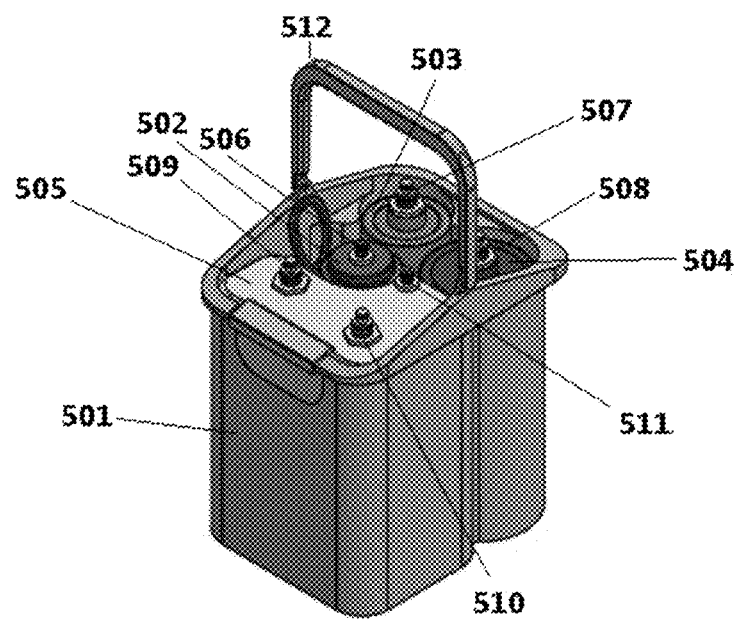
FIG. 11 shows an infusate caddy containing solute containers removed from a dialysis machine.

FIG. 11 shows an infusate caddy 501 removed from a receiving compartment of a dialysis machine. As in FIG. 10, the caddy 501 of FIG. 11 includes cation infusate container 502, sodium bicarbonate container 503 and sodium chloride container 504. Protrusion 513 and protrusion 514 can provide fitting features for the respective receiving compartments for each of the cation infusate container 502, sodium bicarbonate container 503 and sodium chloride container 504. A citric acid container 505 can be optionally added for disinfection after each dialysis session. In a preferred, non-limiting embodiment, an infusate caddy only contains cation infusate container 502, sodium bicarbonate container 503 and sodium chloride container, and does not include a citric acid container. Each of the cation infusate container 502, sodium bicarbonate container 503 and sodium chloride container 504 can be connected to a dialysis system by connectors 506, 507, and 508 respectively. In FIG. 11, the paddles, described in FIG. 10, provide fluid connection between the infusate containers and the dialysis machine. The paddles can be configured so that in the lowered state the paddles align with the connectors of the containers 502, 503 and 504. The caddy 501 can be also configured in a disinfection configuration after use so that the paddles align with citric acid container 505, through connectors 509, 510 and 511. As shown in FIG. 11, the optional handle 512 can be raised for easy carrying of the caddy 501.

Figure 12:
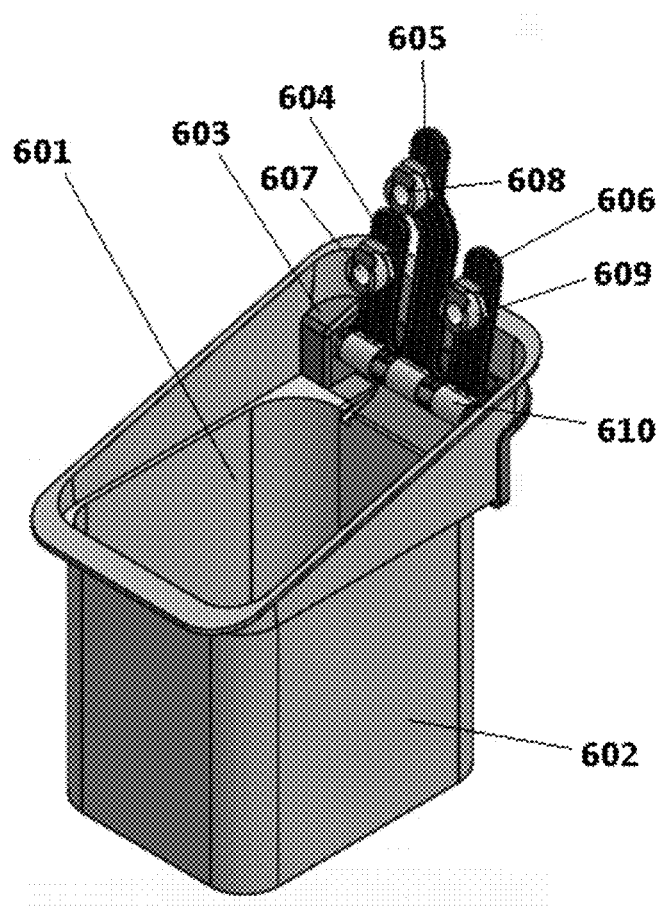
FIG. 12 shows an empty receiving compartment of a dialysis machine with the infusate caddy removed.

FIG. 12 shows an interior 601 and a paddle assembly 603 located at a top section of a receiving compartment 602 with the infusate caddy (not shown) removed. The infusate caddy can be removed from interior 601 of the receiving compartment 602 to replace the containers, refill the containers, store the caddy, clean the caddy, clean the interior 601 of the receiving compartment 602, or for any other reason. The caddy connectors 607, 608, and 609 can be disconnected from the corresponding infusate container fluid connectors as described. The paddles 604, 605, and 606 of the hinged paddle assembly 603 can be raised by pivoting on hinge 610, so that the infusate caddy can be removed from the interior 601. The receiving compartment 602 can be cleaned for reuse with the same or different infusate caddy having an appropriate fitting feature. Curved protrusion 611 can be positioned in at least one of the four corners of the interior 601 of the receiving compartment 602 as a fitting feature for receiving an infusate caddy have a substantially rectangular shaped with curved corners. As described, the fitting feature can include protrusions, indentations, grooves, ridges, size and/or shape, a depth, incline, or diameter to provide complementary surface for an infusate caddy or position of the infusate caddy inside the receiving compartment 602.

Figure 13A:
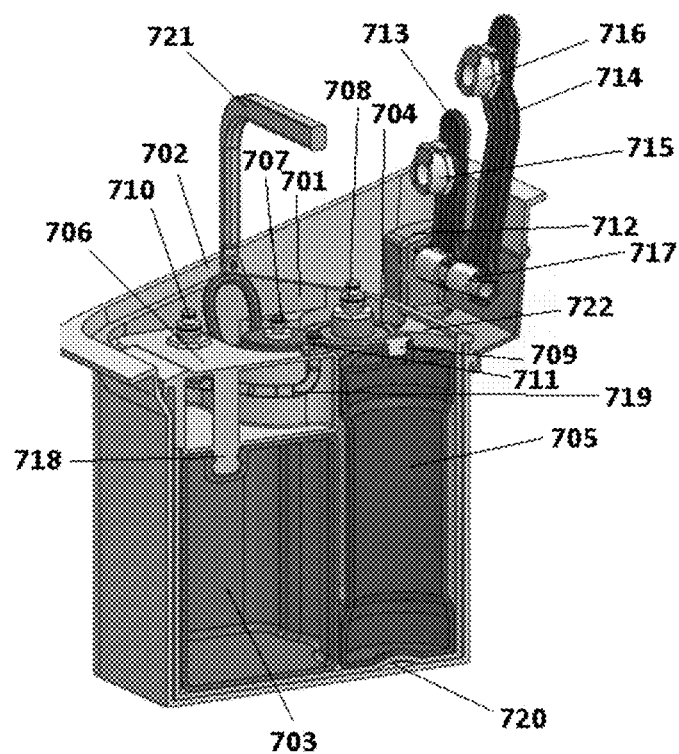
FIG. 13a shows a cut-away view of an infusate caddy containing solute containers in a dialysis machine configured to be used in dialysis.
Figure 13B:
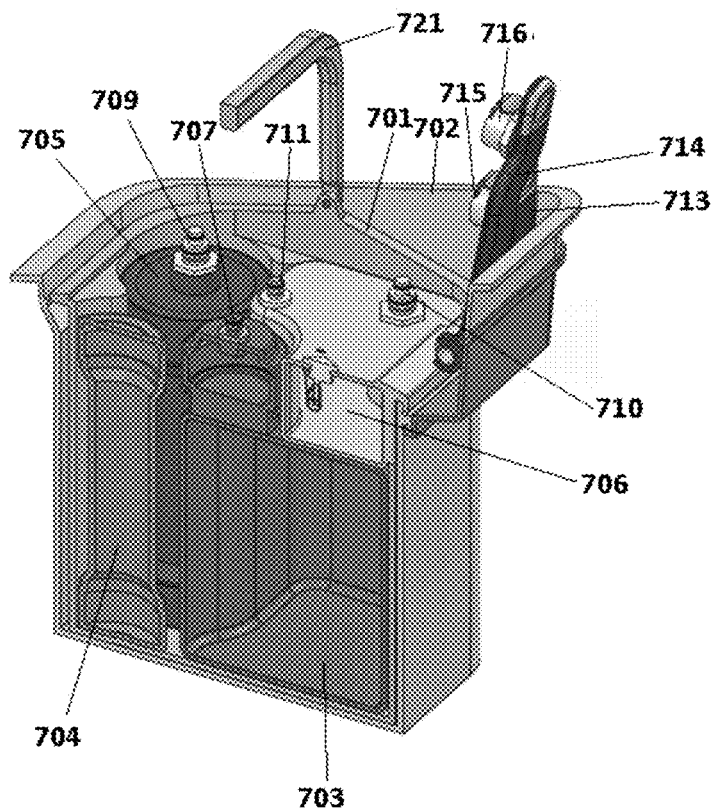
FIG. 13b shows a cut-away view of an infusate caddy containing solute containers in a dialysis machine configured to be used in disinfection.
Figure 13C:
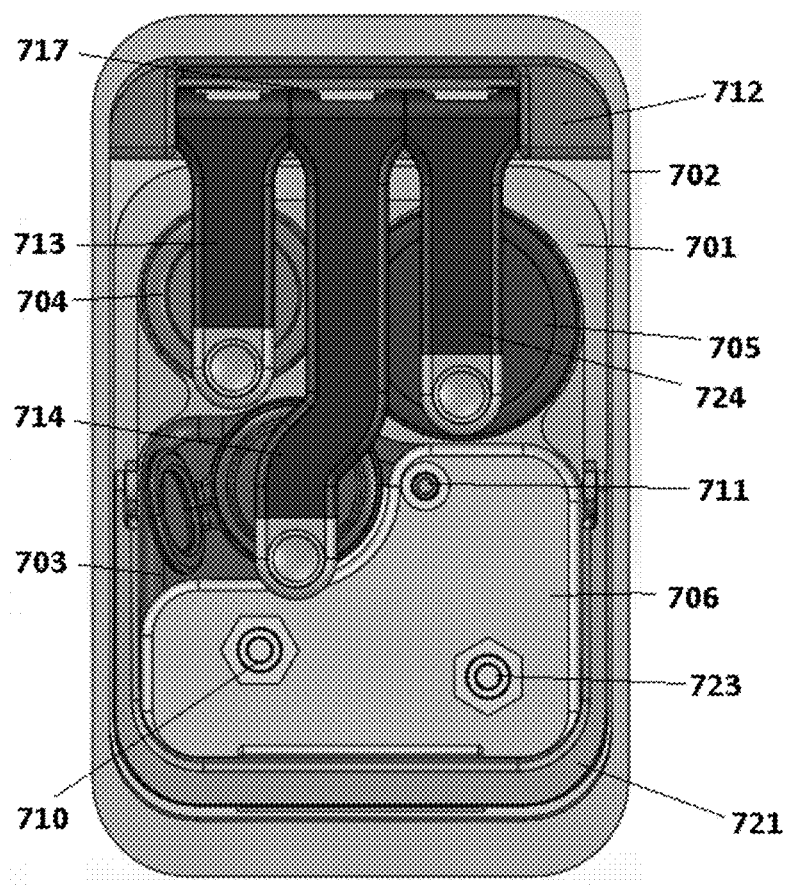
FIG. 13c shows a top view of an infusate caddy containing solute containers in a dialysis configuration seated in a receiving compartment of a dialysis machine.

FIGS. 13a and 13b show cutaway views of a caddy, while FIG. 13c shows a top view of a caddy. Components identified by the same reference numbers in FIGS. 13a, 13b and 13c correspond to the same components. FIG. 13a shows a caddy 701 in a dialysis configuration, or in a priming configuration prior to dialysis, where the caddy 701 is seated in a 702 so the cation infusate container 703, sodium bicarbonate container 704, and sodium chloride container 705 are aligned with the paddles 713 and 714. Citric acid container 706 is not connectable to any paddle in the dialysis configuration of FIG. 13a. Container connector 707 on cation infusate container 703 and container connector 708 on sodium bicarbonate container 704 can connect to fluid connectors 715 on paddle 713 and fluid connector 716 on paddle 714. Fluid connector 709 on sodium chloride container 705 can also connect to a fluid connector (not shown in FIG. 13a). The paddles can be part of paddle assembly 712. To connect the infusate containers to the paddles, the paddles can be rotated downward on hinge 717 and the fluid connectors 715 and 716 can connect to containers 703 and 704 respectively. As shown in FIGS. 13a and 13b, the caddy 701 and the infusate containers within the caddy 701 can have one or more fitting feature to ensure the containers are connected to the correct paddle. The fitting features can also have the additional benefit of ensuring a tight fit within the caddy 701 to resist inadvertent movement. The one or more fitting features can ensure each container occupies a unique position within the caddy 701. Moreover, the interior of the caddy 701 can itself be a shaped fitting feature so each container can only be placed within a specific position or receiving compartment within the caddy 701. Fitting features can be included on any connection surface of the caddy, where any container contacts the interior of the caddy 701. For example, interior of the caddy 701 can include fitting feature protrusion 720, which is a protrusion on the base of the caddy 701. For example, the base of sodium chloride container 705 can be designed with a corresponding complementary indentation, such as a similarly sized recess, while the other containers lack the complementary indentation. Container 705 will be the only container that can properly fit into the position in caddy 701 for protrusion 720. Similarly, curved wedge protrusion 722 is disposed on the side of the caddy 701 interior. The protrusion 722 separates the sidewall of the caddy 701 interior into two sections. Sodium bicarbonate container 704 can be the only container with the proper size, shape, or geometry to fit within one of the sections on the sidewall, whereas sodium chloride container 705 can be the only container with the proper size, shape, or geometry to fit within the other section. Each container can be positioned in one particular location within the caddy 701. Additionally, the containers themselves can have fitting features that ensure the proper arrangement of the containers within the caddy 701. In FIG. 13a, citric acid container 706 includes flange 718. Cation infusate container 703 has a corresponding slot. The citric acid container 706 can only be placed within the caddy 701 at the precise position above cation infusate container 703. By sizing and shaping the interior of the cavity and the containers, the containers can only be placed within the caddy 701 in a single arrangement. When the caddy 701 is seated in the receiving compartment 702, the containers and connectors align with the proper paddles for connection to a dialysis system and related flow path to ensure that the proper solutes from the containers enter the dialysate flow path at the correct locations and that the proper pumps and valves are controlling the correct solute additions. Handle 721 can be included for easy of carrying and removal of the caddy 701 from receiving compartment 702. During use, fluid lines, such as line 719 in citric acid container 706, can move fluids from the containers into the paddles.

The fitting features can include specific types of connectors on the containers and on the paddles or specific locking mechanisms on the paddles adapted for connection to a specific container. For example, connector 707 can be of a specific size, shape, geometry or type, while connector 708 can be of a different size, shape, geometry or type. Correspondingly, fluid connector 716 can be of a complementary size, shape, geometry or type to connector 707, while fluid connector 715 can be of a complementary size, shape, geometry or type to connector 708. In use, fluid connector 716 will only be able to lock onto and form a fluid connection with connector 707, while fluid connector 715 will only be able to lock onto and form a fluid connection with connector 708. That is, each paddle can include a locking mechanism adapted for a particular container, ensuring that the respective containers are connected to the correct paddles for use in dialysis.

FIG. 13*b* shows the caddy 701 in a disinfection configuration. The caddy 701 can be placed in a disinfection configuration by rotating the caddy 701 by 180° degrees so that paddles 713 and 714 align with connectors 709 and 710 on citric acid container 706, which can contain a disinfection solution such as citric acid, placing the paddles 713 and 714 on the opposite side of the caddy 701 as in the dialysis configuration shown in FIG. 13*a*. The same pumps and valves as described for movement of sodium chloride, sodium bicarbonate or cation infusates can be used to direct fluid from the citric acid container 706 into the dialysis system and related flow paths. Fluid lines within the citric acid container 706 can allow circulation between multiple connectors during cleaning or disinfection. For example, fluid can pass between connectors 711 and 710 through citric acid container 706 to allow cleaning or disinfection fluid to be circulated through connectors 715 and 716 by action of a single pump. The caddy 701 can be constructed so that one or more connectors are blocked, and therefore sealed when the caddy 701 is placed in the disinfection configuration. Only the connectors necessary to move citric acid from the citric acid container 706 to the dialysis system can be open to allow fluid movement.

As an alternative to a caddy containing a disinfection container, a second caddy can be used for disinfection. A second caddy, containing a disinfection container, can fit into the dialysis machine in the same receiving slot as the first caddy. The second caddy can include one or more fitting features to ensure that connectors on the disinfection container will align with the paddles or other fluid connectors when the second caddy is inserted into the receiving slot. However, a second caddy is not necessary, and a disinfection container can be directly connected to the fluid connectors for disinfection.

FIG. 13*c* shows a top view of a caddy 701 in a dialysis configuration. As is shown in FIG. 13*c*, sodium chloride container 705 is connected to paddle 724, cation infusate container 703 is connected to paddle 714 and sodium bicarbonate container 704 is connected to paddle 713. Citric acid container 706 is not connected to any paddles in FIG. 13*c*. As shown in FIG. 13*c*, citric acid container 706 includes three connectors 710, 711, and 723. When the caddy 701 is placed in the disinfection configuration, all of the paddles will be connected to citric acid container 706. Paddle 713 can connect to connector 723, paddle 714 can connect to connector 711, and paddle 724 can connect to connector 710. Curved wedge protrusion 728 is a fitting feature to ensure proper placement of sodium bicarbonate container 704 and cation infusate container 703. Curved wedge protrusion 729 is a fitting feature to ensure proper placement of sodium chloride container 705 and citric acid container 706. Similarly, curved corner protrusions 730 at each corner of the receiving compartment 702 can ensure the proper seating of the caddy 701.

Figure 13D:
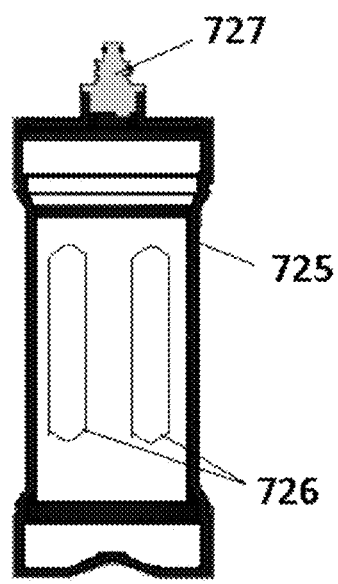
FIG. 13d shows an infusate container with ridges on the exterior of the container to ensure complementary fitting in a caddy.

FIG. 13*d* shows an example of a container wherein the fitting features designed to keep the container in place are a series of ridges. Container 725 can be constructed with one or more ridges 726. The interior of the caddy corresponding to the unique location for container 725 can have a series of complementary corresponding grooves. The container 725 can only be placed in the caddy in the unique position where the complementary grooves in the interior of the caddy align with the ridges 726 on the exterior of the container 725. Other containers can have differently sized ridges, differently spaced ridges, and/or a different number of ridges. The caddy can be constructed with the proper corresponding grooves for each container in the correct location. Because the containers can only be positioned in the caddy where the corresponding ridges and grooves are complementary, these features can ensure the proper position for each container. If the caddy is connected to the dialysis machine, connector 727 on container 725 will align with the proper paddle or other connector on the system to ensure that the proper solution is added to the dialysis system in the proper amounts and at the proper location. One skilled in the art will understand that the grooves can be constructed on the containers and the ridges on the caddy.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. A method for priming a dialysis machine, comprising the steps of:

fluidly connecting two or more detachable infusate containers seated in a removable infusate caddy, the removable infusate caddy having one or more fitting features defining two or more receiving compartments in the infusate caddy; wherein every receiving compartment included in the infusate caddy has a size and/or shape different from every other receiving compartment included in the infusate caddy; each of the at least two receiving compartments in the infusate caddy complementary to one of the two or more detachable infusate containers; each of the two or more detachable infusate containers fitting into one specific receiving compartment defined by the one or more fitting features within the removable infusate caddy, wherein at least one fitting feature on each detachable infusate container is complementary and of a unique size to the one or more fitting features on the removeable infusate caddy; wherein the one or more fitting features of the infusate caddy are configured to define only one arrangement of the two or more detachable infusate containers within the infusate caddy;
selectively opening or closing one or more valves to form a priming flow path in the dialysis machine;
pumping water using one or more pumps into the priming flow path and through two or more detachable fluid connectors into the two or more detachable infusate containers containing one or more solutes;
dissolving the one or more solutes in the two or more detachable infusate containers to form a solution of the one or more solutes inside the two or more detachable infusate containers or adding water to the two or more detachable infusate containers to form the solution of the one or more solutes inside the two or more detachable infusate containers;
selectively opening or closing the one or more valves to form a dialysate flow path in the dialysis machine; and
pumping the solution from the two or more detachable infusate containers into the dialysate flow path to prime the dialysis machine with the one or more solutes.

2. The method of claim 1, wherein the removable infusate caddy is detachable from the dialysis machine.

3. The method of claim 1, wherein the two or more detachable infusate containers comprise any one or more of the group comprising a sodium chloride container, a sodium bicarbonate container, and a cation infusate container.

4. The method of claim 3, wherein the step of pumping the solution from the two or more detachable infusate containers into the dialysate flow path comprises pumping fluid from the sodium chloride container and/or the sodium bicarbonate container to the dialysate flow path downstream of a sorbent cartridge, wherein the one or more valves selectively control the dialysate flow path.

5. The method of claim 4, wherein the step of pumping the solution from the sodium chloride container and/or the sodium bicarbonate container to the dialysate flow path comprises determining an amount of sodium chloride and/or sodium bicarbonate pumped to the dialysate flow path upstream of the sorbent cartridge.

6. The method of claim 5, wherein the step of determining an amount of sodium chloride and/or sodium bicarbonate pumped to the dialysate flow path comprises determining the amount of sodium chloride and/or sodium bicarbonate pumped with a conductivity sensor upstream of the sorbent cartridge.

7. The method of claim 1, wherein at least one of the two or more detachable infusate containers is a disinfection container.

8. The method of claim 3, wherein prior to the step of pumping the water into the priming flow path, the two or more detachable fluid connectors are filled with a disinfectant solution.

9. The method of claim 8, further comprising a step of selectively opening or closing the one or more valves to pump the water from the dialysate flow path to the sodium chloride container and/or to pump the water from the dialysate flow path to the sodium bicarbonate container.

10. The method of claim 8, further comprising partially filling the sodium chloride container and/or the sodium bicarbonate container with the water; wherein a volume of air remains in the sodium chloride container or sodium bicarbonate container.

11. The method of claim 9, further comprising a step of selectively opening or closing the one or more valves to flow air from the sodium chloride container or sodium bicarbonate container to the dialysate flow path while filling the sodium chloride container or sodium bicarbonate container with the water.

12. The method of claim 9, further comprising a step of selectively opening or closing the one or more valves and the one or more pumps to pump the solution from the sodium chloride container or sodium bicarbonate container into the dialysate flow path.

13. The method of claim 12, wherein the amount of the solution pumped from the sodium chloride container to the dialysate flow path is between 10 mL-500 mL.

14. The method of claim 12, further comprising a step of selectively opening or closing the one or more valves to flow air from the sodium chloride container or sodium bicarbonate container to the dialysate flow path and pumping the water from the dialysate flow path to the sodium chloride container or sodium bicarbonate container;
wherein either or both of the sodium chloride container and sodium bicarbonate container is connected to at least two of the two or more detachable fluid connectors, the two or more detachable fluid connectors each having the one or more valves and being fluidly connected to the dialysate flow path.

15. The method of claim 12, wherein an amount of fluid pumped from the dialysate flow path to the sodium bicarbonate container is between 10 mL and 4,000 mL.

16. The method of claim 3, wherein the two or more detachable infusate containers initially contains the one or more solutes that are solid.

17. The method of claim 16, further comprising the step of selectively opening or closing the one or more valves and pumping the water to the two or more detachable infusate containers containing the one or more solutes that are solid to make a solute solution of known concentration.

18. The method of claim 8, further comprising the step of selectively opening or closing the one or more valves to prevent the disinfection solution from entering the two or more detachable infusate containers.

19. The method of claim 12, wherein the steps of pumping the solutions from the sodium chloride container and the sodium bicarbonate container to the dialysate flow path and comprises generating a dialysis fluid with a concentration of solutes suitable for use in dialysis.

20. The method of claim 1, further comprising initiating a dialysis session after priming the dialysis machine, and selectively opening or closing the one or more valves and the one or more pumps to deliver the treatment solutes during the dialysis session to deliver the treatment solutes during the dialysis session with the one or more solutes.

21. The method of claim 1, wherein the two or more detachable fluid connectors are positioned on at least one paddle assembly, the at least one paddle assembly pivoting on a hinge and aligned to fit the two or more detachable fluid connectors to the two or more detachable infusate containers; the two or more detachable fluid connectors fluidly connecting the two or more detachable infusate containers to the dialysate flow path.

22. The method of claim 1, wherein at least one of the two or more detachable infusate containers is fluidly connected to the dialysate flow path both upstream and downstream of a sorbent cartridge; wherein the sorbent cartridge contains urease.

* * * * *